(12) United States Patent
Pyo et al.

(10) Patent No.: US 7,001,744 B2
(45) Date of Patent: Feb. 21, 2006

(54) RECOMBINANT DNA, PLASMID, TRANSFORMED MICROORGANISM AND VACCINE PROTEIN FOR PREVENTION AND THERAPY OF URINARY TRACT INFECTION

(75) Inventors: Suhk-Neung Pyo, Seoul (KR); Yong-Hwa Lee, Seoul (KR)

(73) Assignee: Sungkyunkwan University, Seoul (KR)

( * ) Notice: Subject to any disclaimer, the term of this patent is extended or adjusted under 35 U.S.C. 154(b) by 0 days.

(21) Appl. No.: 10/877,670

(22) Filed: Jun. 25, 2004

(65) Prior Publication Data

US 2005/0232938 A1    Oct. 20, 2005

(30) Foreign Application Priority Data

Apr. 19, 2004    (KR) ...................... 10-2004-0026900

(51) Int. Cl.
*C12P 21/06*    (2006.01)
(52) U.S. Cl. ................... 435/69.1; 530/350; 536/23.1; 424/184.1
(58) Field of Classification Search ............... 435/69.2, 435/69.1; 424/234.1, 184.1; 530/350; 536/23.1
See application file for complete search history.

(56) References Cited

U.S. PATENT DOCUMENTS 5,643,758 A * 7/1997 Guan et al. ................. 435/69.7
2001/0019834 A1 * 9/2001 Kim et al. ................. 435/69.2

OTHER PUBLICATIONS

Pallesen et al., "Chimeric FimH adhesin of Type 1 fimbriae: a bacterial surface display system for heterologous sequences," Microbilogy (1995), 141, 2839-2848.*

* cited by examiner

*Primary Examiner*—Jon Weber
*Assistant Examiner*—Agnes Rooke
(74) *Attorney, Agent, or Firm*—Jordan and Hamburg LLP

(57) ABSTRACT

Disclosed is a novel vaccine against *Escherichia coli* (*E. coli*) responsible for urinary tract infections. The vaccine is a recombinant chimeric protein which is prepared by linking by genetic recombination a gene encoding an antigenic determinant of uropathogenic *E. coli* to a CTXA2B gene encoding nontoxic A2 and B subunits of *Vibrio cholerae* cholera toxin (CTX) or a LTXA2B gene encoding nontoxic A2 and B subunits of *E. coli* heat-labile enterotoxin, wherein a translation product of the CTXA2B or LTXA2B gene serves as an immunogenic adjuvant stimulating mucosal immune responses, expressing the resulting recombinant gene in *E. coli*, and isolating and purifying an expressed recombinant fusion protein. The recombinant chimeric protein is useful as an oral vaccine with mild side effects and excellent vaccination efficiency against uropathogenic *E. coli*. Thus, the chimeric vaccine protein can remarkably reduce recurrence of urinary tract infections, prevent occurrence of antibiotic-resistant bacteria, and replace the conventional chemotherapy for urinary tract infections. Also, the chimeric vaccine protein has other advantages of being capable of being produced and commercialized in a short period with relatively low costs, and being easily modified by replacing its genetic constituents with other genes to provide various vaccines.

14 Claims, 18 Drawing Sheets

FIG. 1

```
attgtaatgaaacgagttattaccctgtttgctgtactgctgatgggctggtcggtaaat  60 bp
 I V M K R V I T L F A V L L M G W S V N                      20 a.a
gcctggtcattcgcctgtaaaaccgccaatggtaccgctatccctattggcggtggcagc 120
 A W S F A C K T A N G T A I P I G G G S                      40
gccaatgtttatgtaaaccttgcgcccgtcgtgaatgtggggcaaaacctggtcgtggat
 A N V Y V N L A P V V N V G Q N L V V D
ctttcgacgcaaatctttttgccataacgattatccggaaccattacagactatgtcaca
 L S T Q I F C H N D Y P E T I T D Y V T
ctgcaacgaggctcggcttatggcggcgtgttatctaattttttccgggaccgtaaaatat
 L Q R G S A Y G G V L S N F S G T V K Y
agtggcagtagctatccattttcctaccaccagcgaaacgccgcgcgttgtttataattcg
 S G S S Y P F P T T S E T P R V V Y N S
agaacggataagccgtggccggtggcgctttatttgacgcctgtgagcagtgcgggcggg
 R T D K P W P V A L Y L T P V S S A G G
gtggcgattaaagctggctcattaattgccgtgcttatttgcgacagaccaacaactat
 V A I K A G S L I A V L R Q T N Y
aacagcgatgatttccagtttgtgtggaatatttacgccaataatgatgtggtggtgcct
 N S D D F Q F V W N I Y A N N D V V V P
actggcggctgcgatgtttctgctcgtgatgtcaccgttactctgccggactaccctggt
 T G G C D V S A R D V T V T L P D Y P G
tcagtgccaattcctcttaccgtttattgtgcgaaaagccaaaacctggggtattacctc
 S V P I P L T V Y C A K S Q N L G Y Y L
tccggcacaaccgcagatgcgggcaactcgattttttcaccaataccgcgtcgttttcacct
 S G T T A D A G N S I F T N T A S F S P
gcacagggcgtcggcgtacagttgacgcgcaacggtacgattattccagcgaataacacg
 A Q G V G V Q L T R N G T I I P A N N T
gtatcgttaggagcagtagggacttcggcggtgagtctgggattaacggcaaattatgca
 V S L G A V G T S A V S L G L T A N Y A
cgtaccggagggcaggtgactgcagggaatgtgcaatcgattattggcgtgacttttgtt
 R T G G Q V T A G N V Q S I I G V T F V
tatcaagaagaacccctggattcatcatgcaccacaaggttgtggaaattcatcaagaaca
 Y Q E E P W I H H A P Q G C G N S S R T
◀FimH | LTXA2 ▶
attacaggtgatacttgtaatgaggagacccagaatctgagcacaatatatctcaggaaa
 I T G D T C N E E T Q N L S T I Y L R K
tatcaatcaaaagttaagaggcagatattttcagactatcagtcagaggttgacatatat
 Y Q S K V K R Q I F S D Y Q S E V D I Y
aacagaattcggaatgaattatgaataaagtaaaatgttatgtttatttacggcgttacta
 N R I R N E L -
                    M N K V K C Y V L F T A L L
    ◀ LTXA2 | LTXB ▶
tcctctctatgtgcatacggagctcccagtctattacagaactatgttcggaatatcgc
 S S L C A Y G A P Q S I T E L C S E Y R
aacacacaaatatatacgataaatgacaagatactatcatatacggaatcgatggcaggc
 N T Q I Y T I N D K I L S Y T E S M A G
aaaagagaaatggttatcattacatttaagagcggcgcaacatttcaggtcgaagtcccg
 K R E M V I I T F K S G A T F Q V E V P
ggcagtcaacatatagactccaaaaaaaagccattgaaggatgaaggacacattaaga
 G S Q H I D S Q K K A I E R M K D T L R
atcacatatctgaccgagaccaaaattgataaattatgtgtatggaataataaaaccccc
 I T Y L T E T K I D K L C V W N N K T P
aattcaattgcggcaatcagtatggaaaactag
 N S I A A I S M E N -
```

FIG. 2

```
atgtaatgaaacgagttattaccctgtttgctgtactgctgatgggctggtcggtaaat      60 bp
 I  V  M  K  R  V  I  T  L  F  A  V  L  L  M  G  W  S  V  N      20 a.a
gcctggtcattcgcctgtaaaaccgccaatggtaccgctatccctattggcggtggcagc    120
 A  W  S  F  A  C  K  T  A  N  G  T  A  I  P  I  G  G  G  S      40
gccaatgtttatgtaaaccttgcgcccgtcgtgaatgtggggcaaaacctggtcgtggat
 A  N  V  Y  V  N  L  A  P  V  V  N  V  G  Q  N  L  V  V  D
ctttcgacgcaaatcttttgccataacgattatccggaaaccattacagactatgtcaca
 L  S  T  Q  I  F  C  H  N  D  Y  P  E  T  I  T  D  Y  V  T
ctgcaacgaggctcggcttatggcggcgtgttatctaattttccgggaccgtaaaatat
 L  Q  R  G  S  A  Y  G  G  V  L  S  N  F  S  G  T  V  K  Y
agtggcagtagctatccatttcctaccaccagcgaaacgccgcgcgttgtttataattcg
 S  G  S  S  Y  P  F  P  T  T  S  E  T  P  R  V  V  Y  N  S
agaacggataagccgtggccggtggcgctttatttgacgcctgtgagcagtgcgggcggg
 R  T  D  K  P  W  P  V  A  L  Y  L  T  P  V  S  S  A  G  G
gtggcgattaaagctggctcattaattgccgtgcttattttgcgacagaccaacaactat
 V  A  I  K  A  G  S  L  I  A  V  L  I  L  R  Q  T  N  N  Y
aacagcgatgattccagtttgtgtggaatatttacgccaataatgatgtggtggtgcct
 N  S  D  D  F  Q  F  V  W  N  I  Y  A  N  N  D  V  V  V  P
actggcggctgcgatgtttctgctcgtgatgtcaccgttactctgccggactaccctggt
 T  G  G  C  D  V  S  A  R  D  V  T  V  T  L  P  D  Y  P  G
tcagtgccaattcctcttaccgtttattgtgcgaaaagccaaaacctggggtattacctc
 S  V  P  I  P  L  T  V  Y  C  A  K  S  Q  N  L  G  Y  Y  L
tccggcacaaccgcagatgcgggcaactcgattttcaccaataccgcgtcgttttcacct
 S  G  T  T  A  D  A  G  N  S  I  F  T  N  T  A  S  F  S  P
gcacagggcgtcggcgtacagttgacgcgcaacggtacgattattccagcgaataacacg
 A  Q  G  V  G  V  Q  L  T  R  N  G  T  I  I  P  A  N  N  T
gtatcgttaggagcagtagggacttcggcggtgagtctgggattaacggcaaattatgca
 V  S  L  G  A  V  G  T  S  A  V  S  L  G  L  T  A  N  Y  A
cgtaccggagggcaggtgactgcagggaatgtgcaatcgattattggcgtgactttgtt
 R  T  G  G  Q  V  T  A  G  N  V  Q  S  I  I  G  V  T  F  V
tatcaagaagagccgtggattcatcatgcaccgccgggttgtgggaatgctccaagatca
 Y  Q  E  E  P  W  I  H  H  A  P  P  G  C  G  N  A  P  R  S
    ◄FimH | cTXA2 ►
tcgatgagtaatacttgcgatgaaaaaacccaaagtctaggtgtaaaattccttgacgaa
 S  M  S  N  T  C  D  E  K  T  Q  S  L  G  V  K  F  L  D  E
taccaatctaaagttaaaagacaaatatttcaggctatcaatctgatattgatacacat
 Y  Q  S  K  V  K  R  Q  I  F  S  G  Y  Q  S  D  I  D  T  H
aatagaattaaggatgaattatgattaaattaaaatttggtgttttttttacagttttacta
 N  R  I  K  D  E  L  -
                          M  I  K  L  K  F  G  V  F  F  T  V  L  L
        ◄ CTXA2 | CTXB ►
tcttcagcatatgcacatggaacacctcaaaatattactgatttgtgtgcagaataccac
 S  S  A  Y  A  H  G  T  P  Q  N  I  T  D  L  C  A  E  Y  H
aacacacaaatacatacgctaaatgataagatattttcgtatacagaatctctagctgga
 N  T  Q  I  H  T  L  N  D  K  I  F  S  Y  T  E  S  L  A  G
aaaagagagatggctatcattacttttaagaatggtgcaacttttcaagtagaagtacca
 K  R  E  M  A  I  I  T  F  K  N  G  A  T  F  Q  V  E  V  P
ggtagtcaacatatagattcacaaaaaaaagcgattgaaaggatgaaggatacctgagg
 G  S  Q  H  I  D  S  Q  K  K  A  I  E  R  M  K  D  T  L  R
attgcatatcttactgaagctaaagtcgaaaagttatgtgtatggaataaaaaacgcct
 I  A  Y  L  T  E  A  K  V  E  K  L  C  V  W  N  N  K  T  P
catgcgattgccgcaattagtatggcaaattaa
 H  A  I  A  A  I  S  M  A  N  -
```

FIG. 3
A
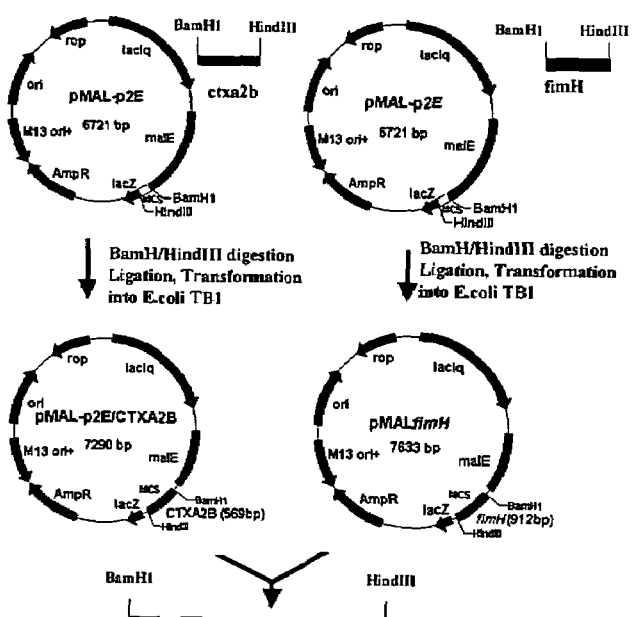
B
C
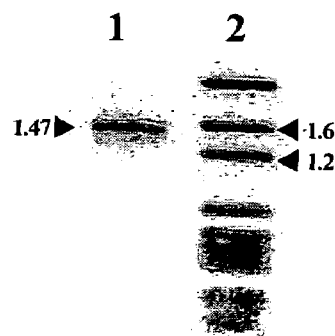

FIG. 4
A
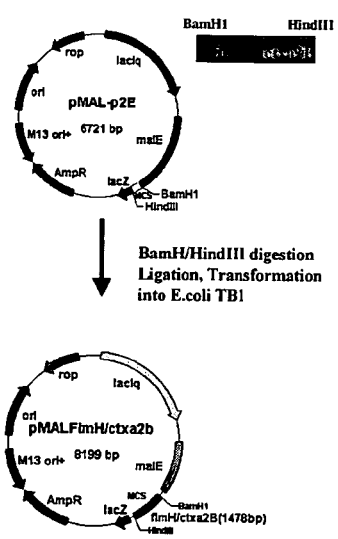
B
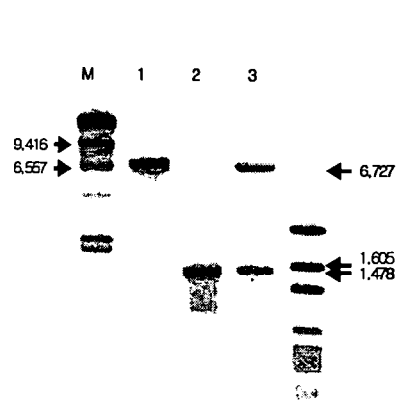
C
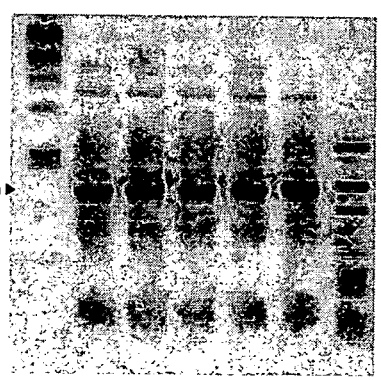

FIG. 5
A
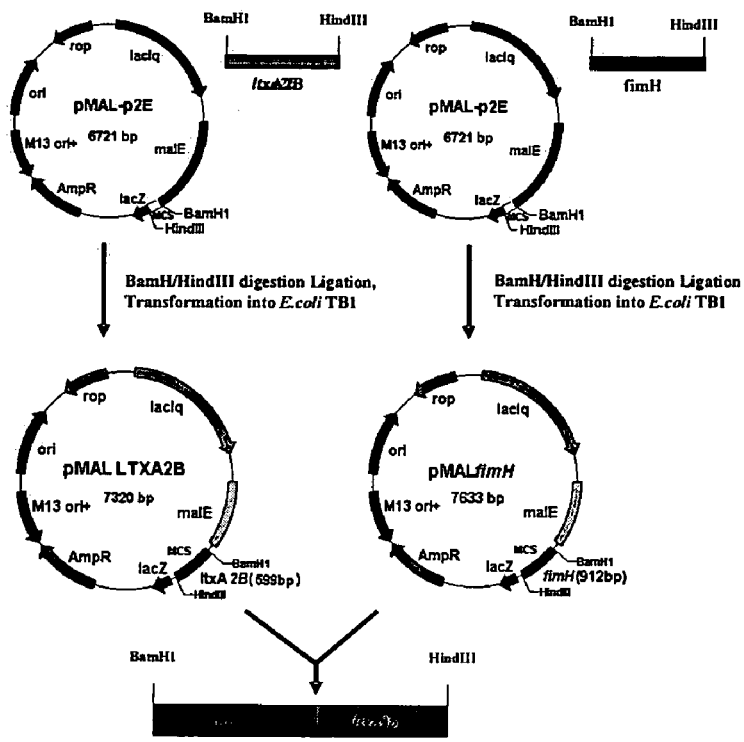
B
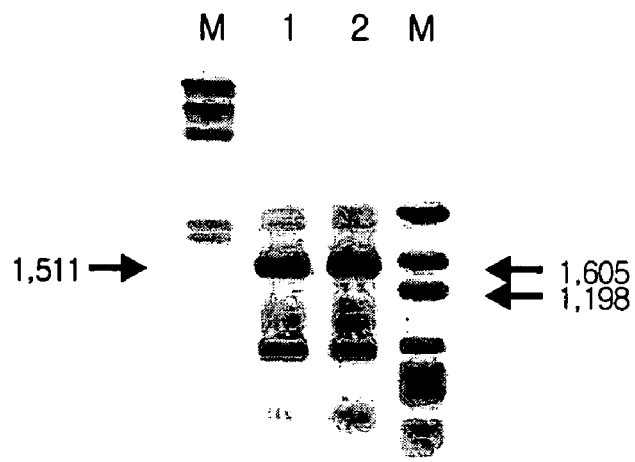

FIG. 6
A
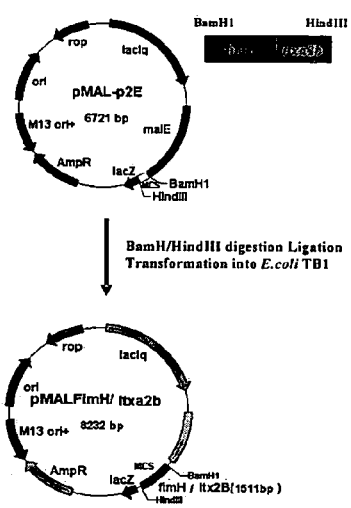
B
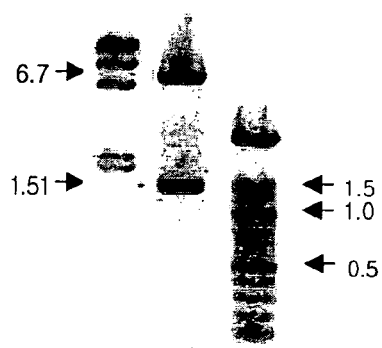
C
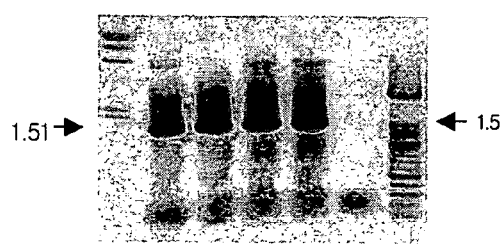

FIG. 9
(A)
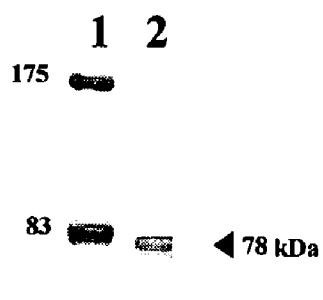
SDS-PAGE
(B)
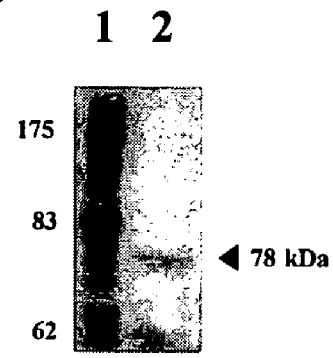
Anti- Adhesin
(C)
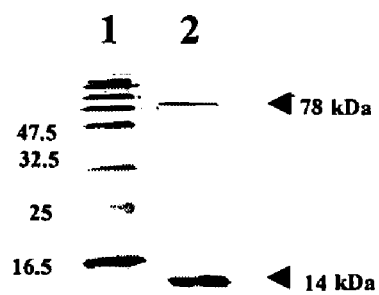
SDS-PAGE
(D)
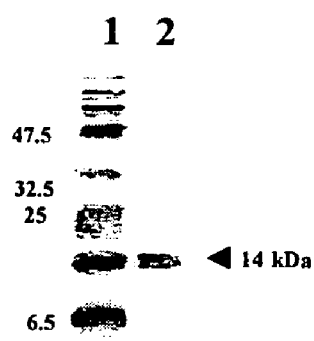
Anti-CTXB

RECOMBINANT DNA, PLASMID, TRANSFORMED MICROORGANISM AND VACCINE PROTEIN FOR PREVENTION AND THERAPY OF URINARY TRACT INFECTION

BACKGROUND OF THE INVENTION

1. Field of the Invention

The present invention relates to a recombinant DNA prepared by linking a gene encoding an antigenic determinant of *Escherichia coli* (*E. coli*) to a CTXA2B gene of *Vibrio cholerae* or a LTXA2B gene of *E. coli*, and an expression plasmid including the recombinant DNA. Also, the present invention is concerned with a microorganism transformed with the expression vector. Further, the present invention relates to a vaccine protein against *E. coli* responsible for urinary tract infections, which is produced by the transformant.

In detail, the present invention relates to a novel vaccine against *E. coli* responsible for urinary tract infections (uropathogenic *E. coli*). The vaccine is a recombinant fusion protein which is prepared by linking by genetic recombination a gene encoding an antigenic determinant of uropathogenic *E. coli* to a CTXA2B gene encoding nontoxic A2 and B subunits of cholera toxin of *Vibrio cholerae* or a LTXA2B gene encoding nontoxic A2 and B subunits of *E. coli* heat-labile enterotoxin, wherein a translation product of the CTXA2B or LTXA2B gene serves as an adjuvant stimulating mucosal immune responses, expressing the resulting recombinant gene in *E. coli*, and isolating and purifying an expressed recombinant chimeric protein.

2. Description of the Prior Art

Urinary tract infections, which are bacterial infections common in the urinary tract, etc., present clinically as cystitis, pyelititis, acute chronic pyelonephritis, and the like (Kunin, 1994; Haley et al., 1985). Diseases caused by bacterial infections of the urinary tract do not exhibit clinical symptoms until a large number of microorganisms proliferate in the urinary tract, and their development frequency follows the most common respiratory tract diseases. Urinary tract infections are reported to be caused by invasion of ascending bacteria through the lower urinary tracts (Patton et al., 1991). Hematogenous infections may occur by *Staphylococcus aureus*, fungi, *Mycobacterium tuberculosis*, etc. Urinary tract infections are caused by various factors including urinary tract obstruction caused by pregnancy, calculus, etc., neurogenic bladder, vesicoureteral reflux, renal diseases, hypertension, diabetes mellitus, catheter insertion, and administration of analgesics and antipyretics (Kunin, 1994). On the other hand, cystitis and nephritis are common in women, while cystitis also occurs frequently in children, and urethritis is common in men (Haley et al., 1985). The urinary tract infections may accompany complications, such as renal papillary necrosis, renal abscess and perirenal abscess (Stamm et al., 1993). About 70% or higher of these urinary tract infections have been known to be caused by *E. coli*. According to some reports, due to these diseases, over seven million people visit primary medical centers every year, and about over one million of them need to be treated in hospitals (Hooton, 2003; Kunin, 1994; Patton et al., 1991). In addition, women are susceptible to the urinary tract infections because their urinary tract has the characteristic structure of being short and wide and is thus easily infected with bacteria. For this reason, women have a 4- to 10-fold higher incidence of the urinary tract infections than men. Over 50% of adult females visit hospitals due to diseases caused by the urinary tract infections, and the majority of the urinary tract diseases is related with recently increased sexual behavior and contraceptive use of menstruating women (Hooton et al., 1996; Kunin, 1994; Stamm et al., 1993; Uehiling et al., 1994).

The urinary tract infections are largely classified into the upper urinary tract infections and the lower urinary tract infections. The upper urinary tract infections, such as pyelonephritis, have symptoms including pyrexia, nausea and vomiting, costovertebral angle tenderness, serum antibody increase and WBC casts. Symptoms of the lower urinary tract infections, such as cystitis and urethritis, include dysuria, polyuria, increased urinary urgency, and suprapubic discomfort (Hooton, 2003).

In addition, according to the infection states, the urinary tract infections are divided into two subcategories: uncomplicated forms (acute uncomplicated cystitis and acute uncomplicated pyelonephritis) and chronic complicated forms (Stamm et al., 1993). The uncomplicated urinary tract infections occur frequently in people in their twenties and thirties suffering from the urinary tract infections. In contrast, the chronic complicated urinary tract infections are common at all ages due to their underlying primary diseases including urolithiasis, hydronephrosis, bladder tumor, vesicoureteral reflux, neurogenic bladder and prostatic hypertrophy, and, in particular, develop frequently in the elderly or men (Gupta et al., 1999b; Haley et al., 1985). The acute uncomplicated cystitis has symptoms including systemic fever, painful urination, increased urinary frequency, haematuria and pyuria by inflammation, and becomes better by proper antibiotic administration (Stamm et al., 1993). However, the acute uncomplicated nephritis has symptoms including high fever, flank pain and bladder irritation, and often exhibits recurrent microbial reinfection after treatment, resulting in transition to chronic infection. About over 60% of the acute uncomplicated nephritis is easily recurrent, and thus, develops to chronic complicated urinary infections accompanied by fever, frequent pyuria and bacteriuria leading to deterioration of renal diseases, and causes focal segmental glomerulosclerosis (FSG) accompanied by proteinuria and necrosis (Kunin, 1994). Further, about 50% of uropathogenic *E. coli* are resistant to kanamycin, and 10% of patients with pyelonephritis and cystitis are reinfected within two to three years. In addition, about 10% of these patients suffer from the diseases all their life due to reinfection (Haley et al., 1985; Hooton et al., 1996).

Treatment of the acute uncomplicated urinary tract infections is carried out with the aim of killing pathogens and reducing reinfection. In particular, the treatment aiming to prevent reinfection has been reported to be very important in treatment of the urinary tract infections. Typically, when not treated for a certain period, the urinary tract infections rapidly recur, and this recurrence is believed to be caused by novel *E. Coli* or bacteria strains. The treatment mainly by antibiotic administration results in disappearance of bacteriuria within 24 hrs, whereas pyuria or other associated symptoms last for several days (Hooton, 2003).

In case of pyelonephritis as another acute uncomplicated urinary tract infection, infections occur in deep regions of the kidney and the urinary epithelium, and, in this case, parenteral treatment is carried out for several days. This parenteral treatment typically takes two weeks or longer. Chemotherapy with trimethoprimsulfamethoxazole (TMP/SMX) (Bactrim®) is more effective than treatment with antibiotics such as ampicillin (Gupta, et al., 1999a, 1999b; Hooton, 2003; Nicolle, 2003). In addition, aminoglycosides, cephalosporins and quinolone are used in therapy of pyelonephritis (Nicolle, 2003).

In case of the chronic complicated infections, treatment is performed by using general antibiotics or chemotherapy, but is highly dangerous because drug administration for a long period increases development of side effects and complications (Kunin, 1994). These treatments have the following problems: (1) emergence of antibiotic-resistant bacteria; (2) an increase in treatment cost by frequent reinfection; and (3) high infection rate (0.5%–0.7% every year). In this regard, there is an increasing need for the development of vaccines effective in treating the urinary tract infections (Hooton et al., 1996; Kunin, 1994; Patton et al., 1991).

To date, there is no commercialized vaccine against uropathogenic E. coli, and only candidate vaccines are at the preclinical stage. Vaccines against uropathogenic E. coli should be prepared by the following development strategy: first, it is preferable that an adhesin essential for bacterial survival is used as a protein antigen; second, a protein antigen should be highly immunogenic and non-toxic; third, a protein antigen should induce mucosal immune responses against a microorganism inhabiting at the junctions between mucosal epithelial cells; fourth, since single use of a protein antigen mostly results in insufficient immune responses, the antigen should be used in combination with an adjuvant capable of enhancing immunogenicity; and, fifth, a protein antigen should be prepared as an oral vaccine convenient upon administration and having no side effects (Service, 1997).

On the other hand, uropathogenic E. coli produces Gal—Gal pili, which participates in its specific attachment to the epithelium of the upper urinary tract, and hemolysin, which is involved in disruption of various cells and intracellular invasion (Roberts et al., 1994). Recently in Korea, using these proteins, vaccine development was attempted by genetic recombination and peptide synthesis, but the vaccine was found to have low antigenicity. In foreign countries, Lagermann et al. (2000) have studied to develop a vaccine using the FimH protein of uropathogenic E. coli by genetic recombination (Kunin, 1994; Patton et al., 1991). The research group recently reported the vaccination effect of FimH against the urinary tract infections in cynomolgus monkeys (Kunin, 1994). According to this report, when MF59 as an adjuvant and FimH were administered to four experimental animals, high vaccination effect was found in three of them. However, in this case, the FimH protein antigen is inconvenient because it should be administered along with the adjuvant to achieve the effective vaccination. In particular, for oral administration, a protein antigen should induce mucosal immune responses and be used essentially along with a nontoxic adjuvant capable of enhancing immunogenicity of a co-administered protein antigen (Foss et al., 1999).

Immune response-associated cells constitute a tissue or organ system to perform effectively their functions, which is called "lymphoid system". The lymphoid system is classified into the primary (or central) lymphoid system (the thymus and the bone marrow), which substantially produces and differentiates lymphocytes, and the secondary (or peripheral) lymphoid system (the spleen, lymph nodes, mucosal lymphoid organs, etc.). The mucosal lymphoid organs amounting to over ⅓ of body lymphoid tissues among the secondary lymphoid system are the place critical for digestion and absorption of a large number of essential nutrients, and function as a physical barrier against harmful impurities and pathogenic microorganisms, and as an immunological barrier important in the body's protective system (Kagnoff et al., 1996). The mucosal lymphoid organs are largely divided into Bronchus-Associated Lymphoid Tissue (BALT) associated with the lung tissue and alveolar cells in the airways, Nasal-Associated Lymphoid Tissue (NALT) localized at the region where the palate is connected to the nose, and Gut-Associated Lymphoid Tissue (GALT) (Kiyono et al., 1996). On the other hand, Bienenstock (1984) suggested expressing together BALT and GALT as "Mucosal Associated Lymphoid Tissue (MALT)". MALT is the largest lymphoid tissue in the body, is present at the mucosal region of the gut, and plays an important role in the protection of the body, including triggering IgA immune response in the gut immune system (Mestecky, 1987). On the other hand, among several immune organs in MALT, Peyer's patches is a major lymphoid tissue in the gastrointestinal tract and is an inductive site for sIgA production, and the GI lumen dome is covered with the flattened epithelium containing M cells specialized for antigen absorption (de Haan et al., 1995; Frey et al., 1997; Roit et al., 1992). The M cells facilitate lymphoid cell activation by transporting captured soluble antigens, bacteria or viruses from the lumen to lymphocytes (Kerneis et al., 1997). That is, lymphocytes in Peyer's patches in the gut are activated by reaction with the antigens ingested by the M cells and then differentiated and maturated in the germinal center of lymphatic follicles. The Peyer's patch lymphocytes move rapidly from the mucosal membrane and activate precursor sIgA$^+$ B cells and CD4$^+$ Th cells, move to the mesenteric lymph node (MLN), and enter the thoracic duct (TD) to arrive in the blood stream and circulate through the body (Kerneis et al., 1997). The circulating cells enter an IgA effector site and transport sIgA. Eventually, the gut immune system including Peyer's patches protects the gut, and regulates systemic inflammation and thus effectively inhibits allergic response, autoimmune diseases, and the like.

Most of vaccine proteins against microorganisms inhabiting musocal surfaces are degraded by GALT, or are not absorbed (de Haan et al., 2000; Kerneis et al., 1997; Kunin, 1994). However, cholera toxin (CTX) produced by Vibrio cholera and heat-labile enterotoxin (LTX) produced by E. coli, which are known to be potent adjuvants stimulating mucosal immune responses, induce strong mucosal immune responses by binding to $G_{M1}$-ganglioside and by tropism of GALT (de Haan et al., 1996; Freytag et al., 1999; Pizza et al., 2001). However, due to toxicity associated with A1 subunit, neither both toxin is used as a mucosal adjuvant in the native form, whereas their variants, A subunit-lacking CTXB and LTXB, or A1 subunit-lacking CTXA2B and LTXA2B are used as adjuvants (Agren et al., 1999; Douce et al., 1999; Haley et al., 1985; Hooton et al., 1996). The CTX A2 and B subunits have been employed in vaccine development. For example, Czerkinsky et al. (1989) genetically replaced the toxic A1 subunit of CTX (CTXA1) by a streptococcal protein adhesin and chemically linked the streptococcal adhesin to CTXB (the nontoxic B subunit of CTX) to provide a vaccine (CTXA2B). In addition, Hajishengallis et al. (1995) and Russell et al. (1991) reported that a genetic recombinant chimeric vaccine, constructed by replacing the CTX A1 subunit (CTXA1) by the saliva-binding region (SBR) of Streptococcus mutans antigen I/II adhesin and linking the SBR to the CTXB by genetic recombination, effectively stimulates the mucosal immune system to secrete secretory IgA antibody (sIgA Ab) via $G_{M1}$-ganglioside and thus effectively prevents pathogenic bacteria from adhering to mucosal surfaces and forming colonies (de Haan et al., 1995; Harokopakis et al., 1998; Lebens et al., 1994; Saito et al., 2001; Tochikubo et al., 1998; Verweij et al., 1998). According to the research associated with a vaccine against Salmonella typhimurium by Harokopakis et al. (1997), a chimeric protein, constructed by replacing CTXA1 by the SBR of a streptococcal protein AgI/II adhesin and linking the SBR to the CTX A2 and B subunits (CTXA2B) by genetic recombination, strongly stimulates serum IgG and IgA antibody responses in mice. According to the research for developing a vaccine against enterotoxigenic *Escherichia coli* (ETEC) strains by Hall et al. (2001), after subjects are immunized with a fusion vaccine, ETEC-CTXB, the proportion of vaccinees showing IgA seroconversion ranged from 70 to 96% in children and from 31 to 69% in adults, while IgG seroconversion was observed in 44 to 75% of the vaccinated children and in 25 to 81% of the vaccinated adults. In addition, an animal test with a chimeric protein formed by genetically linking the hpa adhesin of *Helicobacter pylori* to CTXA2B, conducted by Kim et al. (2001), resulted in an increase in both serum IgA antibody levels as well as sIgA antibody levels in the gastromucosal membrane, demonstrating that the adhesin-CTXA2B chimeric protein is a potential vaccine against *H. pylori*. Further, Lee et al. (2003) reported that a chimeric vaccine constructed by genetically coupling the S1 fragment of pertussis toxin to CTXA2B induces effective vaccination in mice.

In addition, the LTX A2 and B subunits have been employed in vaccine development. For example, Loregian et al. (1999) constructed a chimeric protein (LTXB-Pol) consisting of the LTX B subunit fused to a 27-mer peptide (antiviral peptide) derived from the DNA polymerase of herpes simplex virus 1 (HSV-1) by genetic recombination. Viral DNA synthesis takes place in the nucleus and requires the interaction with an accessory factor, UL42, encoded by the virus. The LTXB-Pol chimeric protein retained the functional properties of both LTXB and peptide components and was shown to inhibit viral DNA polymerase activity in vitro via disruption of the polymerase-UL42 complex. These results indicate that LTXB can be used as a protein carrier and show a potential for HSV vaccine development.

The CTXA2B and LTXA2B subunits have the following advantages as adjuvants: (1) they are able to increase permeability of mucosal epithelial cells (Lycke, 1997); (2) they induce antigen presentation by stimulating MHC class II expression and increasing IL-1 production (Bromander et al., 1991; Millar et al., 2001; Nashar et al., 1993); and (3) they are able to induce mucosal immune responses by stimulating B cells to produce sIgA antibody (Haley et al., 1985; Langermann, 1996; Roit et al., 1992). Therefore, these properties of the adjuvants are applicable to the development of vaccines against the urinary tract infections (Hess et al., 2000).

Many harmful factors are involved in the development and progress of the urinary tract infections caused by *E. coli*, but, first of all, proper colonization of uropathogenic *E. coli* must occur (Kunin, 1994; Patton et al., 1991). The *E. coli* colonization is initiated by attachment to mucosal surfaces via attachment of a specific adhesin of to a specific receptor, mannose, expressed on mucosal surfaces of a host. This colonization of the uropathogenic *E. coli* is limited in infection sites and tissues (Abraham et al., 1985; Beachey et al., 1981; Beachey et al., 1988; Wizemann et al., 1999). On the other hand, the adhesin of *E. coli* is usually composed of proteins in the form of fimbriae or fibrillae, and the receptor to which the specific adhesin of *E. coli* attaches is composed of a glycolipid or glycoprotein (Beachey et al., 1988; Thankavel et al., 1997).

The specific adhesin of the uropathogenic *E. coli* interact in a lock-and-key fashion with a complementary receptor on mucosal surfaces of the host or tissues thereof for colonization (Abraham et al., 1988; Beachy et al., 1988; Jones et al., 1993; Jones et al., 1995; Kunin, 1994). Two classic examples of bacterial adherence to the epithelial cell surfaces are the lipoteichoic acid (LTA)-mediated attachments of Streptococci and the type 1 fimbriae-mediated attachment of *E. coli*. In streptococci, the adhesin, LTA, interacts through its lipid moiety with fibronectin molecules bound to the epithelial cells. In type 1 fimbriated *E. coli*, a minor 29-kDa protein, FimH adhesin, located at the tip of the fimbriae, interacts with D-mannose residues of glycoprotein receptors on host cells (Beachey et al., 1988; Krogfelt et al., 1990). The specific adhesin proteins shown in uropathogenic *E. coli* and other bacteria are known to be highly conserved (Abraham et al., 1988; Kunin, 1994; Palaszynski et al., 1998).

The research using a FimH knockout variant by Langermann et al. (1997) revealed that the surface protein of uropathogenic *E. coli*, FimH, plays a central role in its attachment to the urinary tract and colonization. In a test of this research, when the FimH protein was inhibited, bacterial infection was reduced by over 90%. Many other reports demonstrated that the adhesin proteins on bacteria play important roles in the early phase of their infection process (Jones-Carson et al., 1999; Minion et al., 1986; Palaszynski et al., 1998). In particular, the FimH adhesin, located at the tip of type 1 pili of uropathogenic *E. coli* and other bacteria, specifically interacts with D-mannose residues of glycoprotein receptors on the bladder epithelial tissue, and this interaction is directly involved in bacterial urinary tract infections (Langermann et al., 2001; Knudsen et al., 1998). In particular, the FimH complexed with FimC was suggested as a vaccine candidate capable of preventing the bacterial urinary tract infections. This is because FimC, which serves as a periplasmic chaperone, is critical for proper folding and stabilization of the full-length adhesin (Langermann et al., 2001).

Currently known genes encoding antigenic determinants as virulence factors of uropathogenic *E. coli* include the FimH adhesin of the type 1 pili, which interacts with D-mannose residues of glycoprotein on the mucosal epithelial cells of host cells, PapG adhesin of P-fimbriae (Hultgren et al., 1989), heat-labile toxin (LTX), heat-stable toxin (STX), aerobactin, haemolysin, serum resistance and KI capsule (Abraham et al., 1988; Hutgren et al., 1993).

SUMMARY OF THE INVENTION

Leading to the present invention, with an aim to solve the problems encountered in the prior art, the intensive and thorough research into the development of a vaccine being highly immunogenic against uropathogenic *E. coli*, being stable in the acidic environment of the stomach and stimulating the mucosal immune responses, conducted by the present inventors, resulted in the finding that a chimeric protein, prepared by linking a gene encoding an antigenic determinant of *E. coli* to a CTXA2B gene encoding nontoxic A2 and B subunits of CTX of *Vibrio cholerae* or a LTXA2B gene encoding nontoxic A2 and B subunits of LTX of *E. coli*, can be used as a vaccine against uropathogenic *E. coli*.

It is therefore an object of the present invention to provide a recombinant DNA which is prepared by linking a gene encoding an antigenic determinant of *E. coli* to a CTXA2B gene of *V. cholerae* or a LTXA2B gene of *E. coli*.

It is another object of the present invention to provide an expression plasmid including the recombinant DNA.

It is a further object of the present invention to provide a microorganism transformed with the expression plasmid.

It is a still further object of the present invention to provide a vaccine protein against an uropathogenic E. Coli, which is produced by the transformed microorganism.

BRIEF DESCRIPTION OF THE DRAWINGS

The above and other objects, features and other advantages of the present invention will be more clearly understood from the following detailed description taken in conjunction with the accompanying drawings, in which:

FIG. 1 shows a nucleotide sequence (SEQ ID NO. 6) of a chimeric gene for production of a chimeric vaccine protein against uropathogenic E. Coli, which is prepared by linking by genetic engineering a FimH gene encoding E. coli Fimbriae H to a LTXA2B gene encoding nontoxic A2 (SEQ ID NO: 1) and B (SEQ ID NO: 2) subunits of E. coli heat-labile enterotoxin (LTX), and an amino acid sequence (SEQ ID NO: 4) corresponding to the nucleotide sequence;

FIG. 2 shows a nucleotide sequence (SEQ ID NO: 3) of a chimeric gene for production of a chimeric vaccine protein against uropathogenic E. coli, which is prepared by linking by genetic engineering a FimH gene encoding E. coli Fimbriae H to a CTXA2B gene encoding nontoxic A2 and B subunits of Vibrio cholerae cholera toxin (CTX), and an amino acid sequence (SEQ ID NO: 5) corresponding to the nucleotide sequence;

FIG. 3 shows a schematic process of preparing a chimeric gene for production of a chimeric vaccine protein against uropathogenic E. coli by linking by genetic engineering a FimH gene encoding E. coliFimbriae H to a CTXA2B gene encoding nontoxic A2 and B subunits of Vibrio cholerae cholera toxin (CTX) (A), and results of gel electrophoresis to identify the size of the chimeric gene by restriction mapping (B and C);

FIG. 4 shows a schematic process of inserting a chimeric gene consisting of a FimH gene linked to a CTXA2B gene into an expression vector, pMAL-p2E, by genetic engineering (A), and results of gel electrophoresis to identify the size of the chimeric gene by restriction mapping (B) and PCR (C);

FIG. 5 shows a schematic process of preparing a chimeric gene for production of a chimeric vaccine protein against uropathogenic E. coli by linking by genetic engineering a FimH gene encoding E. coli Fimbriae H to a LTXA2B gene encoding nontoxic A2 and B subunits of E. coli heat-labile enterotoxin (LTX) (A), and a result of gel electrophoresis to identify the size of the chimeric gene by restriction mapping (B);

FIG. 6 shows a schematic process of inserting a chimeric gene consisting of a FimH gene linked to a LTXA2B gene into an expression vector, pMAL-p2E, by genetic engineering (A), and results of gel electrophoresis to identify the size of the chimeric gene by restriction mapping (B) and PCR (C);

FIG. 9 shows results of SDS-PAGE (A and C) and Western blotting (B and D) to identify the size of a FimH/CTXA2B chimeric protein expressed in E. coli and isolated and purified from the periplasmic space by osmotic shock and affinity chromatography, for production of a chimeric vaccine protein against uropathogenic E. coli;

DETAILED DESCRIPTION OF THE INVENTION

Figure 7:
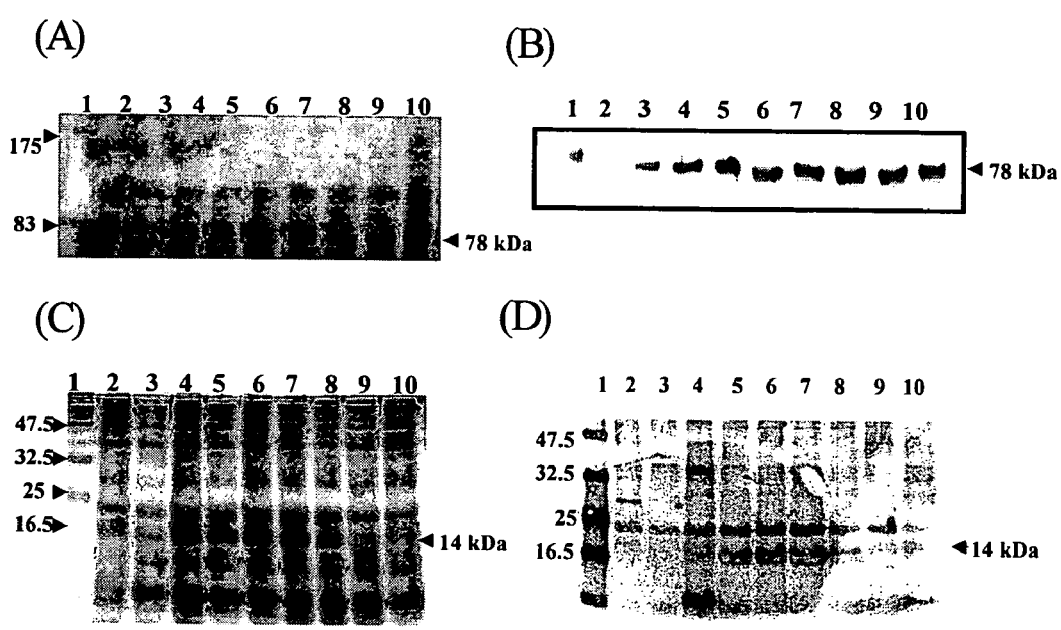
FIG. 7 shows results of SDS-PAGE (A and C) and Western blotting (B and D) to identify the size of a FimH/CTXA2B chimeric protein expressed in E. coli for production of a chimeric vaccine protein against uropathogenic E. coli.

According to an earlier study, oral vaccination with a chimeric protein, which is prepared by linking an adhesin gene of *Streptococcus mutans* to a nontoxic toxin gene (CTXA2B) of *Vibrio cholerae*, resulted in stimulation of production of secretory IgA (sIgA) and serum IgG (Hajishengallis, et al., J. Immunol., 154, 4322 (1995)). However, there is to date no report of vaccines prepared by linking a gene encoding an antigenic determinant of uropathogenic *E. coli* to a nontoxic toxin CTXA2B gene of *Vibrio cholerae* or a nontoxic toxin LTXA2B gene of *E. coli*. Therefore, the present invention is the first to describe preparation of a chimeric vaccine protein by linking a FimH gene of *E. coli* to a CTXA2B gene of *Vibrio cholerae* or a LTXA2B gene of *E. coli*.

70–80% of the urinary tract infections or cystitis in the world is caused by enterobacteria, and recurrence after treatment amounts to over 60%. Thus, *E. coli* becomes resistant to several antibiotics. Also, antibiotics have limitations in use due to their instability to pH, high price, side effects, and the like. In this regard, vaccines capable of preventing and treating *E. coli* infections need to be developed.

Under this situation, the present invention employs an adhesin protein among antigenic proteins of uropathogenic *E. coli* due to its advantages of inducing immune responses, stimulating immunoglobulin production on mucosal surfaces and being essential for colonization of uropathogenic *E. coli* on mucosal surfaces of the urinary tract. Further advantages include that the adhesin protein is non-toxic unlike other antigenic proteins, present in all strains of uropathogenic *E. Coli*, and relatively stable in the urinary tract due to its low molecular weight of 29 kDa in comparison with other protein antigens.

On the other hand, the FimH adhesin, which is a small protein located at the type 1 fimbriae playing a critical role in the bacterial adherence to host cells in the early step of the urinary tract infection process, can induce systemic immune responses, but is difficult to be used alone as a vaccine against uripathogenic *E. Coli* due to its weak mucosal immunogenicity. For this reason, the present invention additionally employs a mucosal adjuvant known to be capable of increasing mucosal immune responses by over two times, that is, CTXA2B or LTXA2B protein that lacks the toxic A1 subunit of cholera toxin (CTX) *Vibrio cholerae* or heat-labile enterotoxin (LTX) of *E. coli*. In the present invention, the FimH adhesin was linked to the CTXA2B or LTXA2B protein by genetic recombination to obtain a chimeric FimH/CTXA2B or FimH/LTXA2B construct. The construct was expressed in *E. coli*. The expressed chimeric protein was isolated and purified, and evaluated for biochemical properties and immunogenicity.

In addition, the isolated chimeric protein was orally administered to mice, and evaluated for its potential as a vaccine against uropathogenic *E. coli* by analyzing antibody production in serum and vaginal fluids obtained from the mice. Also, the CTXA2B or LTXA2B chimeric protein was investigated for its function as an adjuvant.

Further, mice were immunized with the chimeric protein and infected with uropathogenic *E. coli* so as to investigate the preventive effect of the chimeric protein against uropathogenic *E. coli*, wherein the preventive effect was further investigated by histopathological analysis. The therapeutic efficacy of the chimeric protein was investigated in mice infected with uropathogenic *E. coli* and then orally administered with the chimeric protein, and further investigated by histopathological analysis.

The present invention is characterized in that:
(1) a recombinant DNA is prepared by linking a gene encoding an antigenic determinant of *E. coli* to a CTXA2B gene of *Vibrio cholerae*;
(2) a recombinant DNA is prepared by linking a gene encoding an antigenic determinant of *E. coli* to a LTXA2B gene of *E. coli*;
(3) the gene encoding the antigenic determinant of (1) or (2) is FimH;
(4) a recombinant DNA includes a nucleotide sequence of a FimH/CTXA2B chimeric protein, represented by SEQ ID NO. 3 (FIG. 2);
(5) a recombinant DNA includes a nucleotide sequence of a FimH/LTXA2B chimeric protein, represented by SEQ ID NO. 6 (FIG. 1);
(6) an expression plasmid includes the recombinant DNA of (1) or (2);
(7) an expression plasmid includes the nucleotide sequence of (4) or (5);
(8) the expression plasmid of (7) is pMAL-p2E;
(9) a transformed microorganism is prepared by introducing the expression plasmid of (7) into a cell line;
(10) the cell line of (9) is *E. coli*;
(11) in (10), the expression plasmid is pMAL-p2E;
(12) in (10), the transformed microorganism is *E. coli* PSC KCCM-10553 or *E. coli* PSL KCCM-10552;
(13) in (11), the transformed microorganism is *E. coli* PSC KCCM-10553 or *E. coli* PSL KCCM-10552;
(14) a vaccine protein against an uropathogenic *E. coli* is produced by the transformed microorganism of any one of (9) to (13);
(15) a vaccine protein against an uropathogenic *E. coli* includes an amino acid sequence represented by SEQ ID NO. 4 (FIG. 1); and
(16) a vaccine protein against an uropathogenic *E. coli* includes an amino acid sequence represented by SEQ ID NO. 5 (FIG. 2).
(17) a recombinant DNA comprising a nucleotide sequence of a FimH/LTXA2B chimeric protein, which is represented by the combined SEQ ID NOS: 1 and 2, wherein SEQ ID NO: 1 is represented by nucleotides 1–1104 of FIG. 1 and SEQ ID NO: 2 is represented by nucleotides 1101–1475 of FIG. 1.

In order to produce a chimeric protein in *E. coli* using a chimeric DNA composed of an *E. coli* FimH gene linked to a CTXA2B gene of *Vibrio cholerae* or a LTXA2B gene of *E. coli*, the present inventors cloned first by PCR the FimH gene of *E. coli*, the CTXA2B gene of *Vibrio cholerae* and the LTXA2B gene of *E. coli*. Each gene fragment obtained by PCR was digested with BamHI and HindIII, and a FimH gene fragment was ligated to the CTXA2B gene fragment or the LTXA2B gene fragment by T4 DNA ligase. Each of the resulting chimeric DNA molecules and a pMAL-p2E plasmid were digested with BamHI and HindIII, and ligated by T4 DNA ligase. The resulting plasmids were designated pMALfimH/ctxA2B and pMALfimH/ltxA2B, and each of them was introduced into *E. coli* TB1 by the Hanahan D's method (DNA cloning Vol. 1. A practical Approach, IRL press, 1985, 135). The transformants with pMALfimH/ctxA2B and pMALfimH/ltxA2B were expressed as "*E. coli* PSC" and "*E. coli* PSL", respectively, and deposited in the Korean Culture Center of Microorganisms (KCCM) on Jan. 6, 2004, and assigned accession numbers KCCM-10553 and KCCM-10552, respectively.

In accordance with the present invention, the recombinant chimeric protein is useful as an oral vaccine with mild side effects and excellent vaccination efficiency against *E. coli* causing urinary tract infections. Thus, the chimeric vaccine protein may remarkably reduce recurrence of urinary tract infections, prevent occurrence of antibiotic-resistant bacteria, and replace the conventional chemotherapy for urinary tract infections. Also, the chimeric vaccine protein has other advantages of being capable of being produced and commercialized in a short period with relatively low costs, and being easily modified by replacing its genetic constituents with other genes to provide various vaccines.

A better understanding of the present invention may be obtained through the following examples which are set forth to illustrate, but are not to be construed as the limit of the present invention.

EXAMPLE 1

Isolation of Chromosomal DNA from Uropathogenic *E. coli*

An uropathognic *E. coli* was inoculated in tryptic soy broth and cultured at 37° C. for 12 hrs. Chromosomal DNA was isolated from the cultured *E. coli* according to a bacterial chromosomal DNA isolation method.

EXAMPLE 2

Amplification and Cloning of fimH/ctxa2b Chimeric Gene

A fimH/ctxa2b chimeric gene fragment was prepared by PCR using as templates a fimh' gene (924 bp), prepared by adding 12 bases at the upstream of a ctxa2b gene to the downstream of a fimH gene, and a ctxa2b' gene (578 bp), prepared by adding 12 bases at the downstream of a fimH gene to the upstream of a ctxa2b gene, with a oligonucleotide primer set designed to allow for a PCR product to have a BamHI site at its 5' end and a HindIII site at its 3' end. The amplified product was electrophoresed on a 1% agarose gel and stained with EtBr. When the stained DNA was visualized under ultraviolet radiation, a distinct band was found at a position of 1,478 bp predicted from the size of the fimH/ctxa2b chimeric gene (FIG. 3). The amplified fimH/ctxa2b chimeric gene fragment was further confirmed by restriction mapping with DsaI, PstI and SspI. Then, the PCR product was cloned into an expression vector, pMAL-p2E, which was pre-digested with BamHI and HindIII, thus yielding pMALfimH/ctxa2b (FIG. 4A). It was investigated whether the obtained vector contained the successfully cloned PCR product, as follows. The obtained vector was digested with BamHI and HindIII, and the resulting plasmid fragment and insert DNA fragment (fimH/ctxa2b gene fragment) were separated on an agarose gel respectively as a 6,695-bp band corresponding to the plasmid size and a 1,478-bp band corresponding to the fimH/ctxa2b gene size (FIG. 4B). In addition, the insert DNA was further confirmed by PCR using the pMALfimH/ctxa2b as a template and the above oligonucleotide primer set. The PCR product was electrophoresed on a 1% agarose gel and stained with EtBr. When the stained DNA was visualized under ultraviolet radiation, a distinct band was found at the predicted 1,478-bp position (FIG. 4C). The fimH/ctxa2b insert was also confirmed by restriction mapping of the pMALfimH/ctxa2b with DsaI, PstI and SspI. Finally, the fimH/ctxa2b insert was subjected to DNA sequencing analysis using a Sequenase version 2.0 DNA sequencing kit (USB™). Using the obtained nucleotide sequence, an amino acid sequence of the fimH/ctxa2b chimeric gene was obtained. By a nucleotide sequence homology search, the fimH/ctxa2b chimeric gene was found to include a completely identical sequence to the known nucleotide sequences of fimh and ctxa2b genes (Blatter et al., 1997; Domenighimi et al., 1995; Mekalanos et al., 1983). On the other hand, as a result of DNA sequencing, a ctxa2b gene obtained from *Vibrio cholerae* DNA was found to have an overlapped sequence (ATGA) of a stop codon for a ctxa gene and a start codon for a ctxb gene (FIG. 2).

EXAMPLE 3

Amplification and Cloning of fimH/ltxa2b Chimeric Gene

A fimH/ltxa2b chimeric gene fragment was prepared by PCR using as templates a fimH' gene (924 bp), prepared by adding 12 bases at the upstream of a ltxa2b gene to the downstream of a fimh gene, and a ltxa2b' gene (611 bp), prepared by adding 12 bases at the downstream of a fimH gene to the upstream of a ltxa2b gene, with a oligonucleotide primer set designed to allow for a PCR product to have a BamHI site at its 5' end and a HindIII site at its 3' end. The amplified product was electrophoresed on a 1% agarose gel and stained with EtBr. When the stained DNA was visualized under ultraviolet radiation, a distinct band was found at a position of 1,511 bp predicted from the size of the fimH/ltxa2b chimeric gene (FIG. 5). Then, the PCR product was cloned into an expression vector, pMAL-p2E, digested with BamHI and HindIII, thus yielding pMALfimH/ltxa2b (FIG. 6A). It was investigated whether the obtained vector contained the successfully cloned PCR product, as follows. The obtained vector was digested with BamHI and HindIII, and the resulting plasmid fragment and insert DNA fragment (fimH/ltxa2b gene fragment) were separated on an agarose gel respectively as a 6,695-bp band corresponding to the plasmid size and a 1,511-bp band corresponding to the fimH/ltxa2b gene size (FIG. 6B). In addition, the insert DNA was further confirmed by PCR using the pMALfimH/ltxa2b as a template and the above oligonucleotide primer set. The PCR product was electrophoresed on a 1% agarose gel and stained with EtBr. When the stained DNA was visualized under ultraviolet radiation, a distinct band was found at the predicted 1,511-bp position (FIG. 6C). Finally, the fimH/ltxa2b insert was subjected to DNA sequencing analysis using a Sequenase version 2.0 DNA sequencing kit (USB™). Using the obtained nucleotide sequence, an amino acid sequence of the fimH/ltxa2b chimeric gene was obtained. By a nucleotide sequence homology search, the fimH/ltxa2b chimeric gene was found to include a completely identical sequence to the known nucleotide sequences of fimh and ltxa2b genes (Blatter et al., 1997; Domenighimi et al., 1995; Dallas et al., 1980; Domenighini et al., 1995; Spicer et al., 1981). On the other hand, as a result of DNA sequencing, an ltxa2b gene obtained from *E. coli* DNA was found to have an overlapped sequence (ATGA) of a stop codon for an ltxa gene and a start codon for an ltxb gene (FIG. 1).

EXAMPLE 4

*E. coli* Transformation

For large scale preparation of the vector carrying the chimeric gene fimH/ctxa2b or fimH/ltxa2b, prepared in Example 2 or 3, competent cells were prepared using an *E. Coli* strain DH5α, as follows. *E. coli* DH5α was inoculated in 7 ml of LB liquid medium and incubated with agitation at 37° C. for 12–14 hrs. 1 ml of the culture was inoculated again in 50 ml of LB liquid medium, incubated with agitation until the culture reached an $OD_{600}$ of 0.5 to 0.6, and then placed on ice for 5 min. 30 ml of the second culture was transferred to a sterilized tube and centrifuged at 12,000×g for 5 min at 4° C. The supernatant was discarded, and the cell pellet was resuspended in 15 ml of ice-cold 50 mM $CaCl_2$ by gentle tapping and placed on ice for 15 min. After the cell suspension was centrifuged at 12,000×g at 4° C. for 5 min, the supernatant was discarded, and the cell pellet was resuspended in 3 ml of ice-cold 50 mM $CaCl_2$ and placed on ice for 3 hrs, thus giving competent cells. Then, 2 μl of the vector carrying the chimeric gene fimH/ctxa2b or fimH/ltxa2b, prepared in Example 2 or 3, was added to 200 μl of the competent cells, and incubated on ice for 30 min. After heat shock at 42° C. for 90 sec, the cells were incubated on ice for 2 min. The cells were supplemented with 1 ml of LB medium, and subsequently incubated with agitation at 200×g for one hour. Then, the cells were centrifuged at 7,000×g, and 1 ml of the supernatant was discarded, and the cell pellet was resuspended using the residual medium. 10 μl and 100 μl of the cell suspension were individually smeared onto LB solid medium containing an antibiotic, and incubated at 37° C. overnight. Separately, for protein expression, an *E. coli* strain K12 TB1 was transformed according to the same method as described above. 10 μl and 100 μl of the transformed cells were individually smeared onto LB solid medium containing an antibiotic, and incubated at 37° C. for over 18 hrs. In case that the vector had a β-gal gene at its cloning site, the transformed cells were grown on LB solid medium containing an antibiotic and X-gal, and white colonies formed were picked and cultured in a large scale. The cloned *E. coli* transformants containing the pMALfimH/ctxa2b and the pMALfimH/ltxa2b were expressed as "*E. coli* PSC" and "*E. coli* PSL", respectively, and deposited in the Korean Culture Center of Microorganisms (KCCM) on Jan. 6, 2004, and assigned accession numbers KCCM-10553 and KCCM-10552, respectively.

EXAMPLE 5

Polymerase Chain Reaction (PCR)

Figure 8:
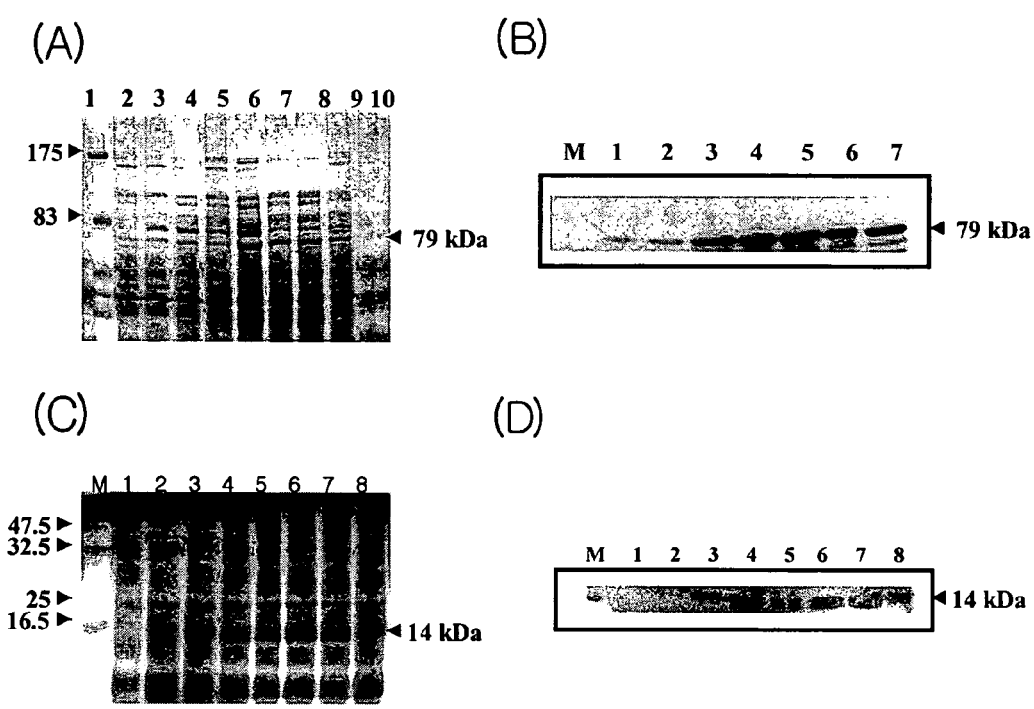
FIG. 8 shows results of SDS-PAGE (A and C) and Western blotting (B and D) to identify the size of a FimH/LTXA2B chimeric protein expressed in E. coli for production of a chimeric vaccine protein against uropathogenic E. coli.
Figure 10:
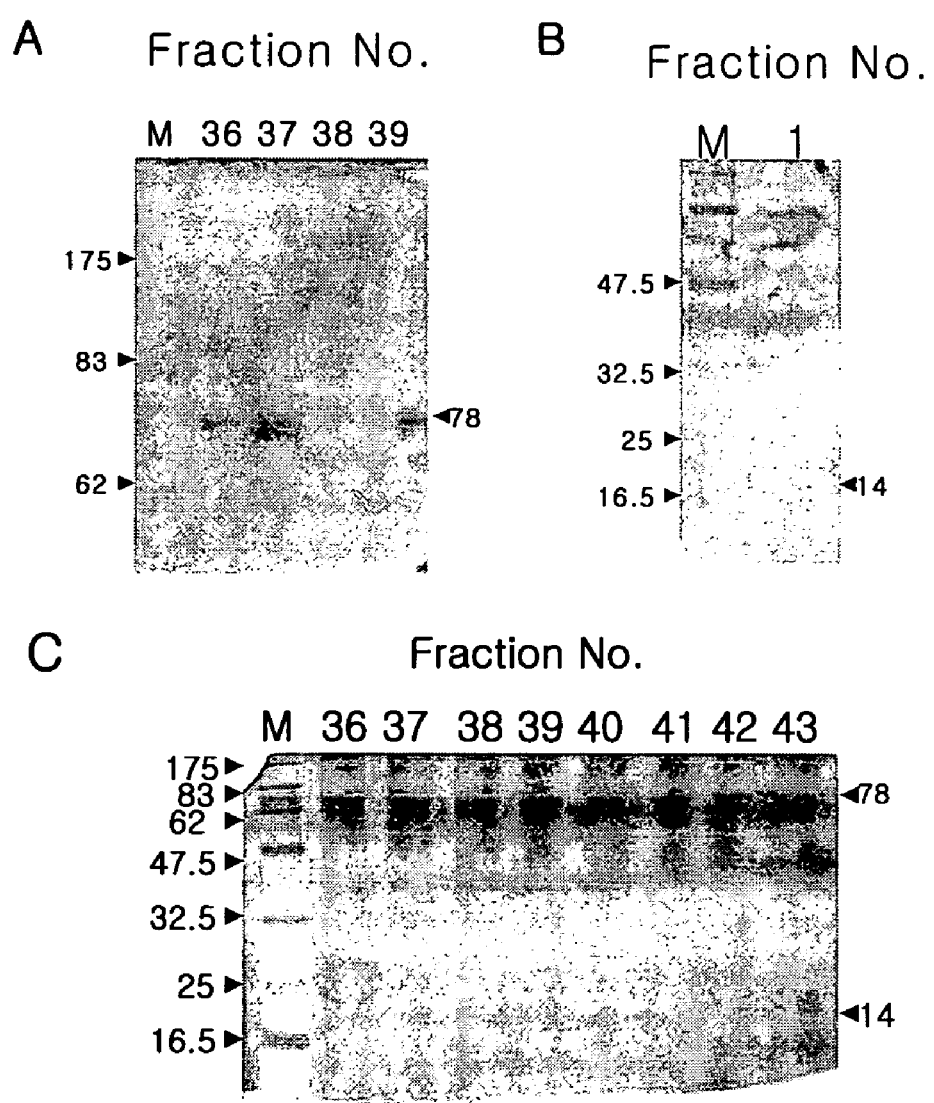
FIG. 10 shows results of SDS-PAGE (C) and Western blotting (A and B) to identify the size of a FimH/LTXA2B chimeric protein expressed in E. coli and isolated and purified from the periplasmic space by osmotic shock and affinity chromatography, for production of a chimeric vaccine protein against uropathogenic E. coli.
Figure 11:
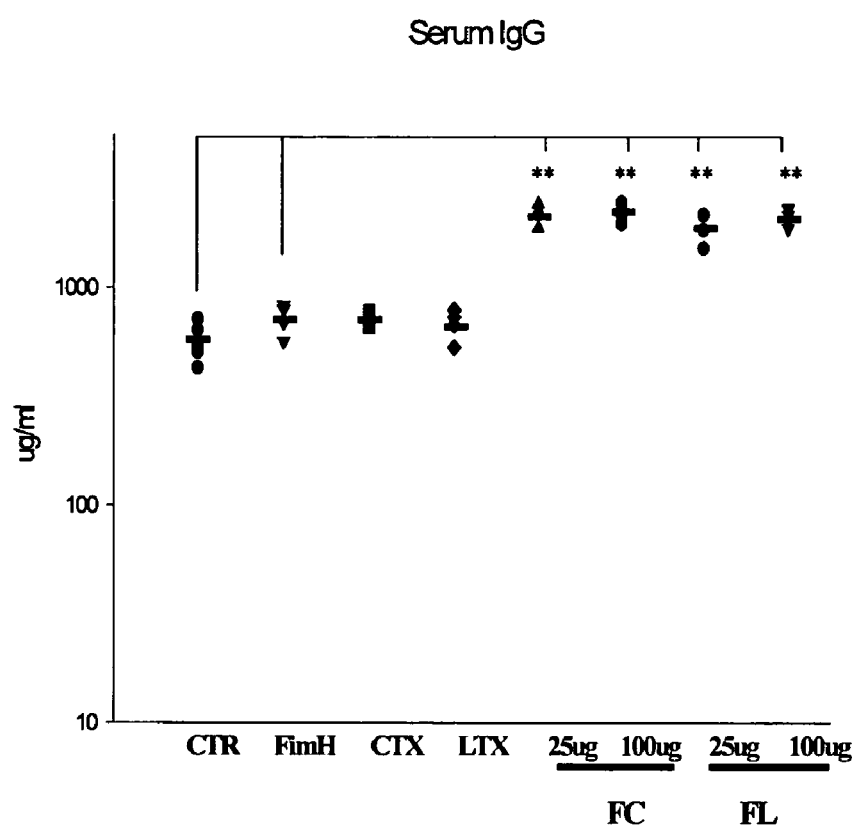
FIG. 11 shows serum sIgA antibody levels in female BALB/c mice orally administered with FimH/CTXA2B or FimH/LTXA2B chimeric proteins to investigate immunogenicity of the chimeric proteins.
Figure 12:
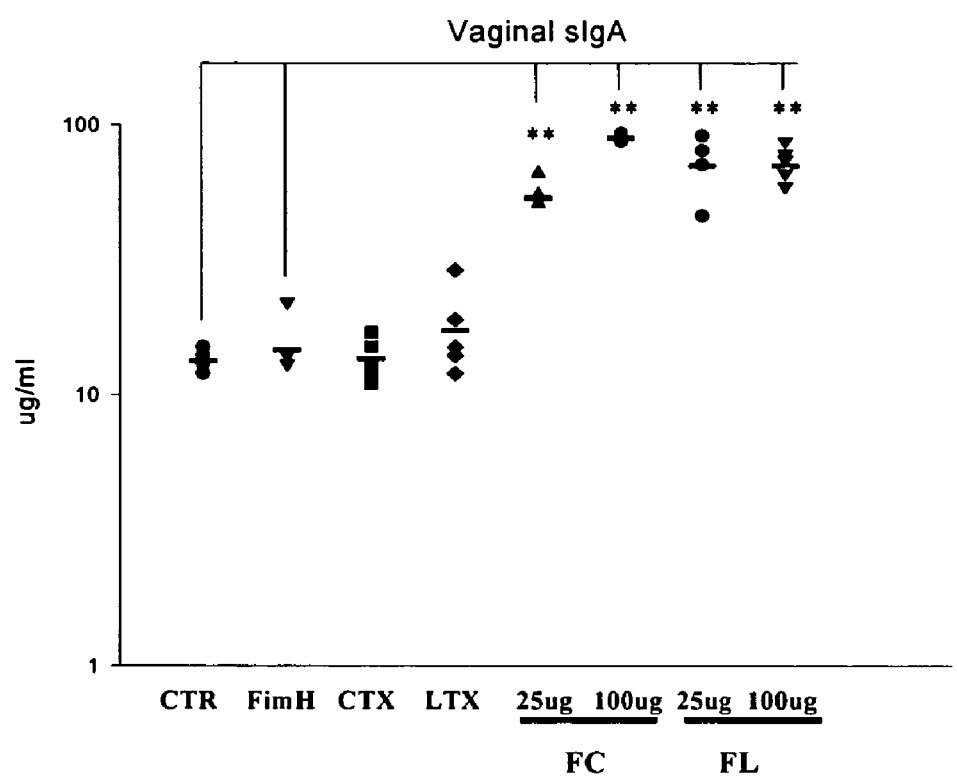
FIG. 12 shows sIgA antibody levels in virginal mucosal fluids of female BALB/c mice orally administered with FimH/CTXA2B or FimH/LTXA2B chimeric proteins to investigate immunogenicity of the chimeric proteins.

The fimH/ctxa2b chimeric gene was prepared by PCR using fimH' and ctxa2b' genes of 50 ng as templates, 20 pmole of primers, 0.25 mM dNTPs, pfu polymerase (Takara, Japan) and a High Fidelity PCR Kit (Boehringer Mannheim, U.S.A.). PCR conditions included denaturation at 94° C. for 120 sec, 10 cycles of denaturation at 94° C. for 10 sec, annealing at 55° C. for 60 seq and extension at 72° C. for 60 sec, and 20 cycles of denaturation at 94° C. for 15 sec, annealing at 58° C. for 30 seq and extension at 72° C. for 180 sec, followed by final extension at 72° C. for 420 sec. The PCR products were stored at 4° C.

The fimH/ltxa2b chimeric gene was prepared by PCR using fimH' and ltxa2b' genes of 50 ng as templates according to the same method as described in the case of fimH/ctxa2b, except for first annealing at 54° C. for 60 sec, second annealing at 58° C. for 30 sec and final extension at 72° C. for 160 sec.

EXAMPLE 6

$G_{M1}$-Ganglioside ELISA

Since the B subunit of each of the cholera toxin (CTX) and the *E. coli* heat-labile enterotoxin (LTX) specifically interacts with monosialoganglioside $G_{M1}$, ELISA is typically utilized to quantitatively analyze CTX and LTX, in particular, CTXB and LTXB. $G_{M1}$-ganglioside ELISA was carried out, as follows. $G_{M1}$-ganglioside was diluted with PBS to a concentration of 1 μg/ml, and 100 μl of the dilution was added to each well of an ELISA plate and incubated at room temperature overnight. Each well was washed with PBS three times, and, after water was completely removed, was added with 200 μl of a blocking solution (1% BSA in PBS). After incubation at 37° C. for one hour, each well was washed with PBS three times and added with 100 μl of a diluted sample, followed by incubation at 37° C. for 2 hrs. After being washed with PBS, each well was added with 100 μl of a 1:2,000 dilution of a primary antibody (anti-CTX goat antibody, Biogenesis Co., 2060–0004) and incubated at 37° C. for 2 hrs. After being washed with PBS, each well was added with 100 μl of a 1:5,000 dilution of a secondary antibody (anti-goat IgG alkaline phosphatase-conjugated antibody, Sigma Co., A4187) and incubated at 37° C. for 2 hrs. After being washed with PBST, each well was added with 100 μl of a para-nitrophenylphosphate (pNPP) solution and incubated at 37° C. for 30 min. Absorbance was measured at 405 nm using an ELISA reader.

EXAMPLE 7

Expression of FimH/CTXA2B and FimH/LTXA2B Chimeric Proteins

To express the FimH/CTXA2B and FimH/LTXA2B chimeric proteins in *E. coli*, first, the *E. coli* TB1 transformed with the pMALfimH/ctxa2b was grown in 0.2% glucose-containing LB medium. When the culture reached an $OD_{600}$ of 0.5 to 0.6, IPTG was added to the culture medium at various concentrations of 0.01, 0.05, 0.1, 0.3, 0.5 and 1.0 mM to induce gene expression. On 0, 2, 4, 6, 8, 10, 12, 24 and 48 hrs after IPTG induction, the cell culture was collected, and protein samples obtained from the collected cells were electrophoresed on 7% and 15% SDS-PAGE gels and stained with Commassie Blue. An about 78-kDa band and an about 14-kDa band were observed at all of the various collection times after the IPTG induction, which were believed to correspond corresponded respectively to a MBP (maltose binding protein; 42.2 kDa)-linked FimH/CTXA2 (36 kDa) fusion protein and a CTXB protein (FIGS. 7A and 7C). This expression pattern demonstrates that, when cloned into an expression vector and expressed in bacteria, the fimH/ctxa2b chimeric gene are translated to two separate polypeptides by an identical message in the same manner as in the ctx operon, as described by Mekalnos et al. (1983). The two bands visualized by Commassie Blue staining were identified as the MBP/FimH/CTXA2 protein and the CTXB subunit, respectively, by immunoblotting assay on a single SDS-PAGE gel using antibodies to MBP and CTXB (FIGS. 7B and 7D). In addition, $G_{M1}$-ganglioside ELISA was carried out to investigate cellular localization of the expressed chimeric protein. As a result, the FimH/CTXA2B chimeric protein was found to be expressed mainly in a soluble form and be transported to the periplasmic space.

In addition, the FimH/LTXA2B chimeric protein was expressed in *E. coli* according to the same method as described above. Protein samples obtained were electrophoresed on 7% and 15% SDS-PAGE gels and stained with Commassie Blue. An about 78-kDa band and an about 14-kDa band were observed at all of the various times after the IPTG induction, which were believed to correspond respectively to a MBP (42.2 kDa)-linked FimH/LTXA2 (37 kDa) fusion protein and a CTXB protein (FIGS. 8A and 8C). This expression pattern demonstrates that, when cloned into an expression vector and expressed in bacteria, the fimH/ltxa2b chimeric gene is translated to two separate polypeptides from an identical message in the same manner as in the ctx operon. The two bands visualized by Commassie Blue staining were identified as the MBP/FimH/LTXA2 protein and the LTXB subunit, respectively, by immunoblotting assay on a single SDS-PAGE gel using antibodies to MBP and LTXB (FIGS. 8B and 8D). In addition, $G_{M1}$-ganglioside ELISA was carried out to investigate cellular localization of the expressed chimeric protein. As a result, the FimH/LTXA2B chimeric protein was found to be expressed mainly in a soluble form and be transported to the periplasmic space.

EXAMPLE 8

Isolation and Purification of the Chimeric Proteins

To produce the FimH/CTXA2B and FimH/LTXA2B chimeric proteins using the *E. coli* TB1 transformant containing the pMALfimH/ctxa2b or pMALfimH/ltxa2b plasmid and to isolate and purify the expressed chimeric proteins, the transformant was grown under optimal conditions for protein production in a 2-liter scale, thus generating 23 mg and 34 mg total proteins. Protein isolation from the periplasmic space was carried out by an osmotic shock method as described by Neu et al. (1965) and amylose resin affinity chromatography according to the protocol supplied by its manufacturer (pMAL$_{TM}$ Protein Fusion and Purification System, New England Biolabs, INC, USA). When fractions collected were analyzed by measuring absorbance at 280 nm, fractions 23 to 28 for FimH/CTXA2B and fractions 36 to 44 for FimH/LTXA2B were found to contain proteins. The selected protein fractions were analyzed by $G_{M1}$-ganglioside ELISA. Fractions 18 to 22 for FimH/CTXA2B and fractions 29 to 34 for FimH/LTXA2B showed $G_{M1}$-ganglioside activity. In addition, to determine purity of the purified proteins and whether they are present in native forms, the protein fractions with $G_{M1}$-ganglioside activity were concentrated using an Amincon centriprep concentrator, and subjected to SDS-PAGE (FIGS. 7A and 7C) and Western blotting with antibodies to MBP, CTX and LTX. As a result, the purified FimH/CTXA2B chimeric protein showed both 78-kDa band (corresponding to MBP/FimH/CTXA2) and 14-kDa band (corresponding to CTXB monomer) (FIGS. 9B and 9D). Also, in case of the purified FimH/LTXA2B chimeric protein, both 81-kDa band (MBP/FimH/LTXA2) and 14-kDa band (LTXB monomer) were found by SDS-PAGE (FIG. 10C) and Western blotting (FIGS. 10A and 10B). The amount of the purified proteins was determined by a Bradford method. The FimH/CTXA2B and FimH/LTXA2B chimeric proteins were found to be produced in *E. coli* in yields of 0.6 mg and 0.8 mg, respectively, per 2-liter culture.

EXAMPLE 9

Evaluation of Immunogenecity of FimH/CTXA2B and FimH/LTXA2B Chimeric Proteins

6–8 week-old BALB/c mice were divided into six groups each of which consisted of six mice, and immunized three times every ten days, as follows. The mice were orally administered through a sonde with both 100 $\mu$g of FimH/CTXA2B, 25 $\mu$g of FimH/LTXA2B, 200 $\mu$g of FimH protein, 20 $\mu$g of CTXA2B or 20 $\mu$g of LTXA2B. Mice orally administered with PBS (phosphate buffered saline, pH 7.2) were used as a control. All of the mice were starved for two hours before administration and one hour after administration. Seven days after the third immunization, mice were sacrificed, and blood samples were collected. Serum IgG antibody levels were measured by ELISA.

When compared to the control group, the FimH treatment group, the CTXA2B treatment group and the LTXA2B group, both groups administered with FimH/CTXA2B and FimH/LTXA2B chimeric proteins showed a very significant increase in serum IgG antibody levels (FIG. 11).

To investigate the effect of the purified FimH/CTXA2B and FimH/LTXA2B chimeric proteins on mucosal sIgA antibody responses, 6–8 week-old female BALB/c mice were divided into eight groups each of which consisted of six mice, and immunized three times every ten days, as follows. The mice were orally administered with 100 $\mu$g of FimH/CTXA2B, 100 $\mu$g of FimH/LTXA2B, 25 $\mu$g of FimH/CTXA2B, 25 $\mu$g of FimH/LTXA2B, 100 $\mu$g of FimH protein, 20 $\mu$g of CTXA2B, 20 $\mu$g of LTXA2B, or PBS as a control. Mucosal fluid samples were collected by washing the vagina of the mice. The mice were intraperitoneally injected with pentobarbital of 100 mg/kg three days before the vaginal washing. After the mice were anesthetized, their vagina was washed with 50 $\mu$l of PBS using a micropipette, and the PBS was then recovered and centrifuged. The supernatant was analyzed for mucosal sIgA antibody levels by ELISA. This sampling was carried out ten days after the third immunization. When compared to the control group, the FimH treatment group, the CTXA2B treatment group and the LTXA2B treatment group, both groups administered with the FimH/CTXA2B and FimH/LTXA2B chimeric proteins showed a very significant increase in mucosal sIgA antibody levels (FIG. 12).

EXAMPLE 10

Evaluation of Antibody Production by ELISA

An antigen was diluted to a concentration of 30 $\mu$g/ml, and 100 $\mu$l of the dilution was placed into each well of a 96-well Nunc Immunoplate (MaxiSorp U16j Nunc, Roskilde, Denmark), followed by incubation at 37° C. for one day. Each well of the plate was washed with PBST buffer containing 0.05% Tween 20, added with 200 $\mu$l of a blocking solution containing 1% BSA in PBS, and incubated at 37° C. for two hours. After each well was washed with the PBST buffer three times, 100 $\mu$l of a 1:10 dilution of each of the samples obtained by the vaginal washing and the serum samples was added to each well. After reaction at room temperature for one to two hours, each well was washed with the PBST buffer three times, and treated with 100 $\mu$l of a 1:1,000 dilution in a 1% BSA buffer of each of alkaline phosphatatase-conjugated anti-mouse IgG, IgA and IgM antibodies, at room temperature for one to two hours. Each well was washed with the PBST buffer three times, and treated with 100 μl of p-nitrophenylphosphate (pNPP) at room temperature for 30 min (Elson et al., 1984). Then, absorbance at 405 nm was measured using an automatic microplate reader (Molecular device, U.S.A.).

EXAMPLE 11

Evaluation of Vaccination Efficacy of the FimH/CTXA2B and FimH/LTXA2B Chimeric Proteins Vaccination efficacy of the FimH/CTXA2B and FimH/LTXA2B chimeric proteins against uropathogenic E. coli was evaluated by investigating an uropathogenic E. coli infection in mice immunized with FimH/CTXA2B (100 μg), FimH/LTXA2B (100 μg), FimH (200 μg), CTXA2B (20 μg) or LTXA2B (20 μg).

Female BALB/c mice were divided into six groups each of which consisted of six mice, and immunized three times every ten days by oral administration using a sonde. A control group was orally administered with PBS. Ten days after the third immunization, 50 μl of an uropathogenic E. coli strain J96 ($5 \times 10^7$ CFU/ml) was injected to the bladder through the urinary tract using a sterile 24-gauge Teflon catheter (outer diameter: 0.7 mm; length: 19 mm; Becton Dickinson Infusion Therapy System, Inc., Sandy, Utah) (Asahara et al., 2001; Hopkins et al., 1995; Jones-carson et al., 1999). Three days after infection, the mice were sacrificed, and the bladder was excised from each mouse, immersed in 1 ml of PBS, and ground using a homogenizer (ULTRA-TURRAX T25). The ground bladder was diluted with PBS by ten times, and 100 μl of the dilution was smeared onto a selection solid medium for uropathogenic E. coli J96. After incubation at 37° C. for one day, the formed colonies were counted. To evaluate the effect of the FimH/CTXA2B and FimH/LTXA2B chimeric proteins on preventing uropathogenic E. coli infections, the colony number of the group vaccinated with both FimH/CTXA2B and FimH/LTXA2B chimeric proteins was compared to that of the control group and the groups immunized with the single protein.

Figure 13:
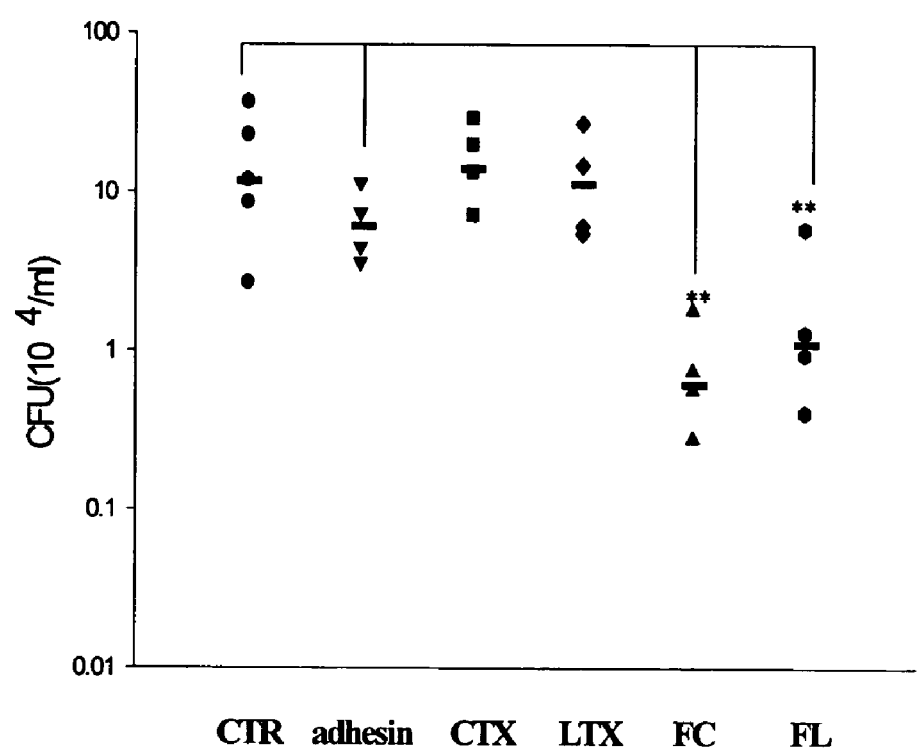
FIG. 13 shows colony numbers of an uropathogenic E. coli in female BALB/c mice which have been immunized by oral administration with FimH/CTXA2B or FimH/LTXA2B chimeric proteins and the bladder of which has been then injected with the E. coli via the urinary tract to investigate preventive effect of the chimeric proteins against E. coli urinary tract infections.

The control group was found to be infected with E. coli J96 of $2.3 \times 10^5$ CFU/ml, the FimH treatment group with $8.8 \times 10^4$ CFU/ml, the FimH/CTXA2B group with $8.2 \times 10^3$ CFU/ml, and the FimH/LTXA2B group with $9.4 \times 10^3$ CFU/ml. As apparent from the data, when both groups administered with the chimeric proteins in a dose of 100 μg were compared to the control group and the FimH treatment group, the FimH/CTXA2B and FimH/LTXA2B chimeric proteins were found to have excellent preventive effect against E. coli urinary tract infections (FIG. 13).

EXAMPLE 12

Histopathological Study

Figure 14:
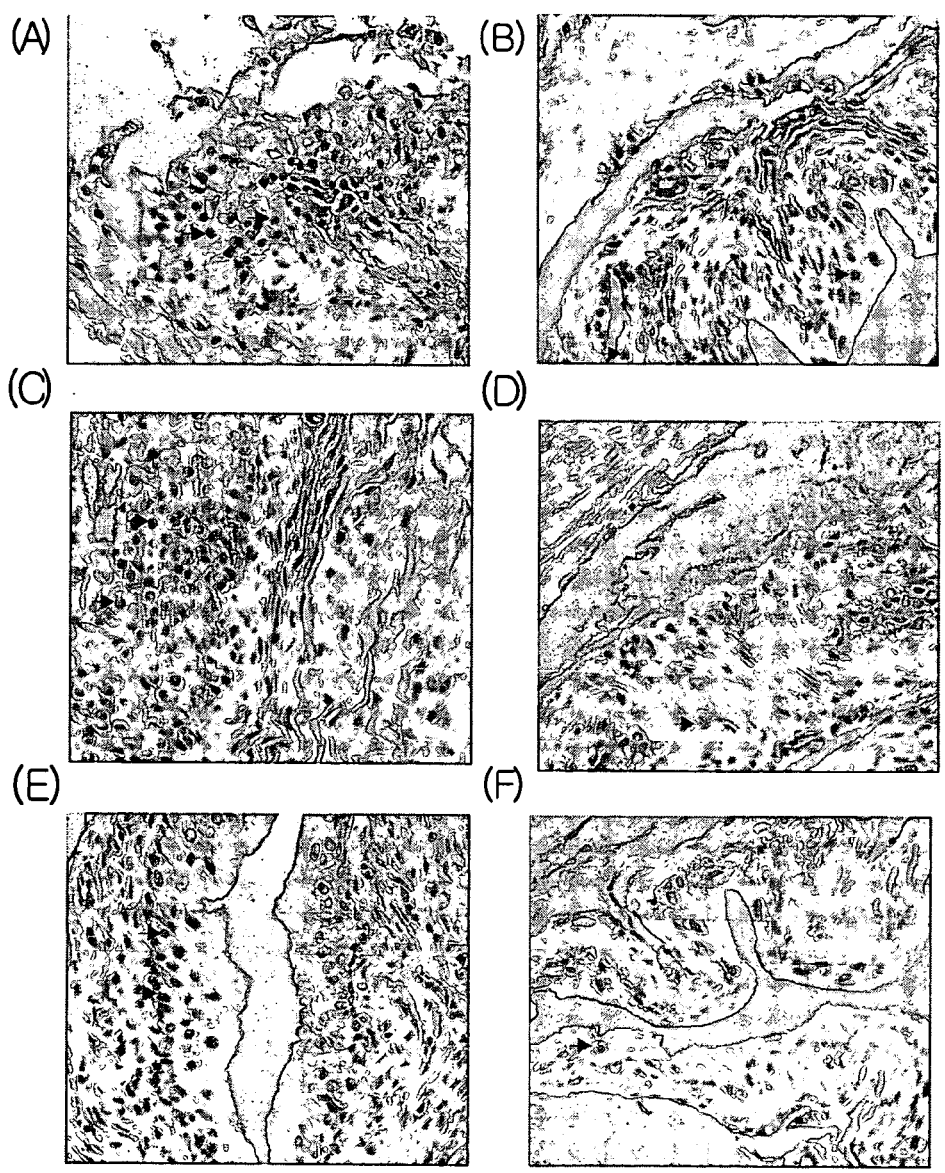
FIGS. 14 A–F shows results of H&E staining as a histopathological study for neutrophils, as one of immune cells most quickly infiltrating infection sites, in the bladder mucosal layer of female BALB/c mice which have been immunized by oral administration with FimH/CTXA2B or FimH/LTXA2B chimeric proteins and the bladder of which has been then injected with an uropathogenic E. coli via the urinary tract to investigate preventive effect of the chimeric proteins against E. coli urinary tract infections.

The FimH/CTXA2B and FimH/LTXA2B chimeric proteins was further investigated for their vaccination effect against uropathogenic E. coli by a histological study. The bladder was excised from mice immunized with the chimeric proteins and then infected with uropathogenic E. coli, and subjected to H&E staining to determine an increase in neutrophils that are one of immune cells most quickly infiltrating to the site of inflammation in the bladder. In a control, a large number of neutrophils gathered around the mucosal surfaces (FIG. 14-A). In CTXA2B and LTXA2B treatment groups, a large number of neutrophils also gathered around the mucosal surfaces in the similar level to the control group (FIGS. 14-C and 14-E). By contrast, in a FimH treatment group, a relatively smaller number of neutrophils were found in comparison with the control group (FIG. 14-B). On the other hand, in chimeric protein treatment groups, neutrophils were rarely found around the mucosal surfaces (FIGS. 14-D and 14-F). These results indicate that the chimeric proteins induce IgG and sIgA antibody responses to the co-administered antigen, leading to neutralization of the bacteria or failure of bacterial adherence to mucosal surfaces of the urinary tract, and inflammation thus does not occur in the bladder.

Figure 15:
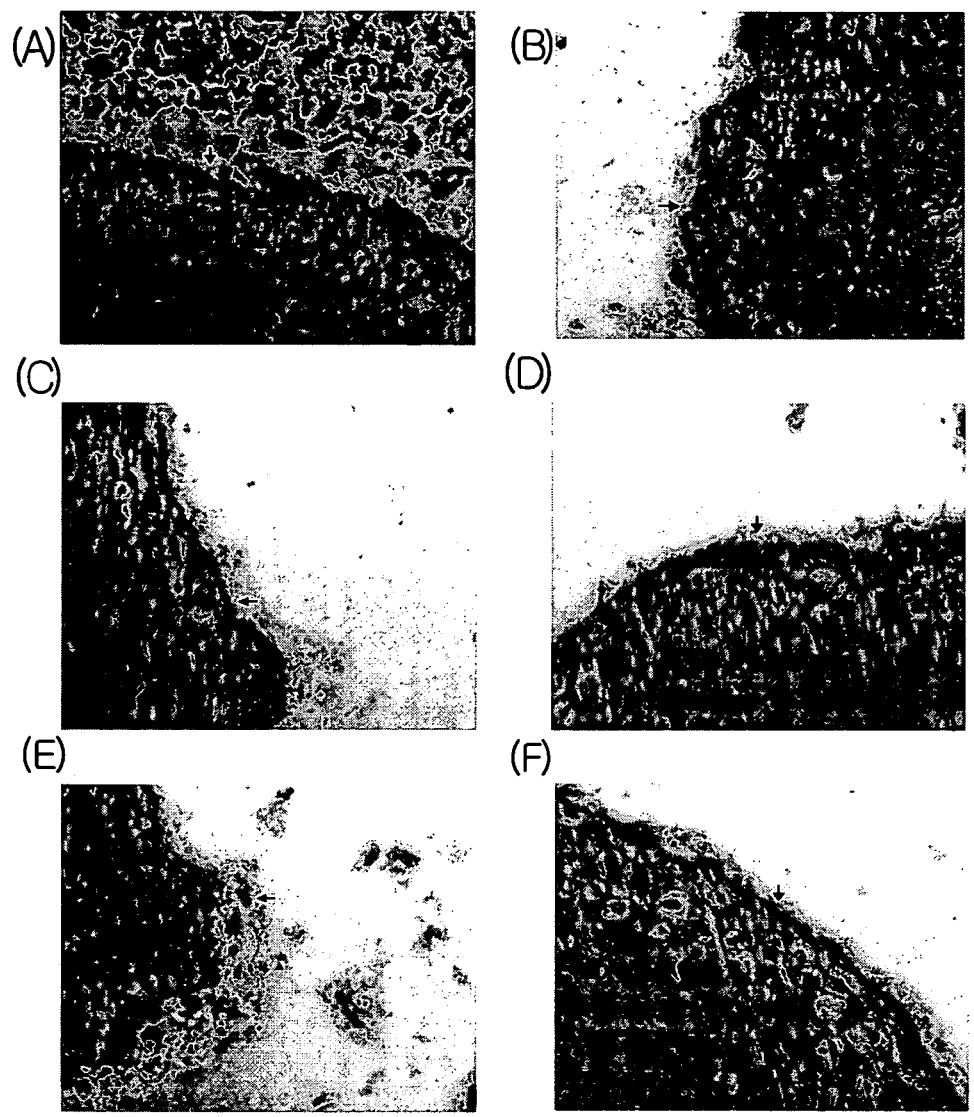
FIGS. 15 A–F shows results of Gram staining as a histopathological assay for E. Coli in the bladder mucosal layer of female BALB/c mice which have been immunized by oral administration with FimH/CTXA2B or FimH/LTXA2B chimeric proteins and the bladder of which has been then injected with an uropathogenic E. coli via the urinary tract to investigate preventive effect of the chimeric proteins against E. coli urinary tract infections.

In addition, Gram staining was carried out to investigate the degree of bacterial adherence around the bladder mucosal surfaces. In the control, a dense colony crowd of the uropathogenic E. coli was found along the mucosal layer (FIG. 15-A). In the CTXA2B and LTXA2B treatment groups, a large number of neutrophils also gathered along the mucosal layer in the similar level to the control group (FIGS. 15-C and 15-E). By contrast, in the FimH treatment group, a relatively smaller number of neutrophils gathered along the mucosal surfaces in comparison with the control group (FIG. 15-B). Further, in the chimeric protein treatment groups, a great reduction in neutrophil number was found around the mucosal surfaces (FIGS. 15-D and 15-F).

EXAMPLE 13

Myeloperoxidase (MPO) Assay

MPO assay is a quantification marker for neutrophils that are one of immune cells most quickly infiltrating to the site of inflammation. To further investigate the protective effect of the chimeric proteins against uropathogenic E. coli by MPO assay, female BALB/c mice were divided into six groups each of which consisted of six mice, and immunized three times every ten days by oral administration using a sonde with FimH/CTXA2B (100 μg), FimH/LTXA2B (100 μg), FimH (200 μg), CTXA2B (20 μg) and LTXA2B (20 μg). A control group was orally administered with PBS. 50 μl of an uropathogenic E. coli strain J96 ($5 \times 10^7$ CFU/ml) was injected to the bladder through the urinary tract using a sterile 24-gauge Teflon catheter (outer diameter: 0.7 mm; length: 19 mm; Becton Dickinson Infusion Therapy System, Inc., Sandy, Utah). Three days after infection, the mice were sacrificed, and the bladder was excised from each mouse, immersed in 1 ml of PBS, and ground using a homogenizer (ULTRA-TURRAX T25). After the ground bladder was centrifuged, the pellet was added with 500 μl of 0.5% HTAB (Hexaadecyltrimethyl-ammnounium Bromide) in PBS and sonicated for 10 sec on ice. The sonicated product was centrifuged at 10,000×g, and the supernatant was recovered (Haraoka et al., 1999). 10 μl of the cell extract was aliquotted into a 96-well plate, and 100 μl of a mixture of TMB (0.1 mg/ml tetramethylbenzidine dihydrochloride) and 0.05 M phosphate citrate buffer (pH 5.0) in an equal ratio was added to each well of the plate. When a desired color development was achieved, absorbance at 650 nm was measured using a microplate reader.

Figure 16:
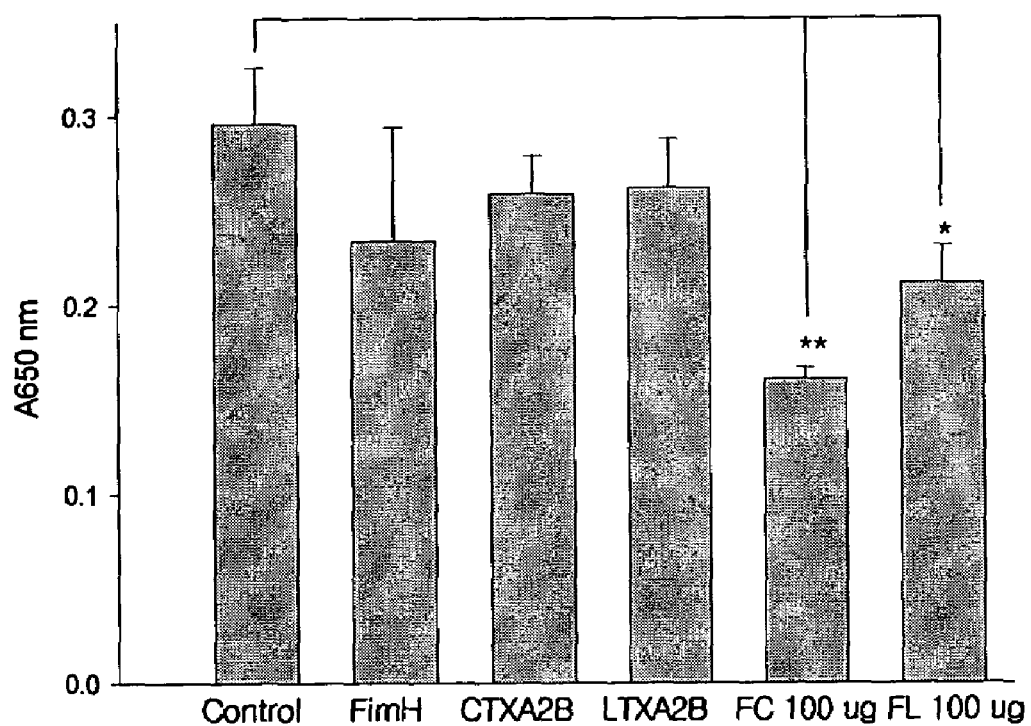
FIG. 16 shows results of MPO assay as a histopathological study for quantification of neutrophils, as one of immune cells most quickly infiltrating infection sites, in the bladder mucosal layer of female BALB/c mice which have been immunized by oral administration with FimH/CTXA2B or FimH/LTXA2B chimeric proteins and the bladder of which has been then injected with an uropathogenic E. coli via the urinary tract to investigate preventive effect of the chimeric proteins against E. coli urinary tract infections.

Compared to the control group, both FimH/CTXA2B and FimH/LTXA2B chimeric protein treatment groups showed a significant reduction in the number of neutrophils (FIG. 16). These results demonstrate that the chimeric proteins have a potential as a vaccine against uropathogenic E. coli. When uropathogenic E. coli infects the urinary tract, a large number of neutrophils and leukocytes in blood vessels in the bladder mucosal region gather at the infection sites, and immune responses are increased at the sites by the immune cells, leading to serious inflammation and eventually tissue damage. In this situation, a reduction in the number of neutrophils indicates that a substance administered has preventive effect against the infection.

EXAMPLE 14

Evaluation of Therapeutic Efficacy of the FimH/CTXA2B and FimH/LTXA2B Chimeric Proteins The FimH/CTXA2B and FimH/LTXA2B chimeric proteins were evaluated for therapeutic efficacy against uropathogenic *E. coli* infections, as follows.

Female BALB/c mice were divided into six groups each of which consisted of six mice, and infected with 50 µl of an uropathogenic *E. coli* strain J96 ($5 \times 10^7$ CFU/ml) was injected to the bladder through the urinary tract using a 24-gauge Teflon catheter (outer diameter: 0.7 mm; length: 19 mm; Becton Dickinson Infusion *Therapy System*, Inc., Sandy, Utah) (Asahara et al., 2001; Hopkins et al., 1995; Jones-carson et al., 1999). One day after infection, mice were orally administered using a sonde with FimH (200 µg), CTXA2B (20 µg), LTXA2B (20 µg), with FimH/CTXA2B (100 µg) or FimH/LTXA2B (100 µg), and the oral administration was carried out twice more, eight days after the first administration and five days after the second administration. A control group was orally administered with PBS. Three days after the third oral administration, the mice were sacrificed, and the bladder was excised from each mouse, immersed in 1 ml of PBS, and ground using a homogenizer (ULTRA-TURRAX T25). The ground bladder was diluted with PBS by ten times, and 100 µl of the dilution was smeared onto a selection solid medium for uropathogenic *E. coli* J96. After incubation at 37° C. for one day, the formed colonies were counted. To evaluate the effect of the FimH/CTXA2B and FimH/LTXA2B chimeric proteins on preventing uropathogenic *E. coli* infections, the colony number of the group administered with the FimH/CTXA2B or FimH/LTXA2B chimeric protein was compared to that of the control group and the groups immunized with the single protein.

Figure 17:
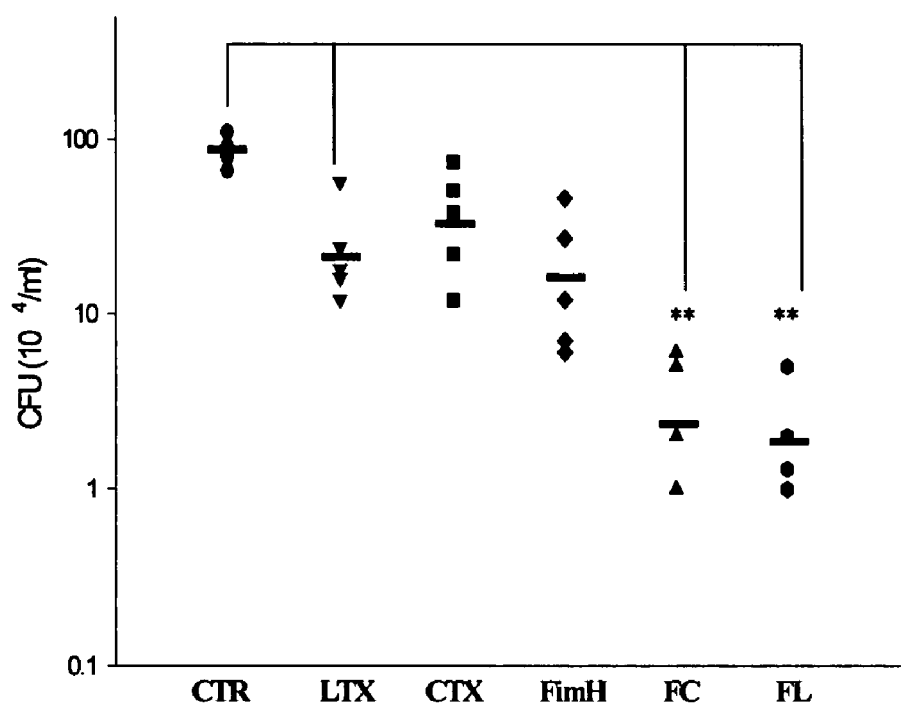
FIG. 17 shows colony numbers of an uropathogenic E. coli in female BALB/c mice the bladder of which has been then directly injected with the E. coli via the urinary tract and which has been then immunized by oral administration with FimH/CTXA2B or FimH/LTXA2B chimeric proteins to investigate therapeutic effect of the chimeric proteins against E. coli urinary tract infections.

The control group was found to be infected with *E. coli* J96 of $8.8 \times 10^5$ CFU/ml, the FimH treatment group with $3.4 \times 10^5$ CFU/ml, the FimH/CTXA2B group with $2.4 \times 10^4$ CFU/ml, and the FimH/LTXA2B treatment group with $1.3 \times 10^4$ CFU/ml. Compared to the control group and the FimH treatment group, in the groups administered with the chimeric proteins in a dose of 100 µg, the *E. coli* urinary tract infection was greatly alleviated (FIG. 17). These results indicate that the chimeric proteins have excellent therapeutic efficacy versus *E. coli* urinary tract infections.

EXAMPLE 15

Figure 18:
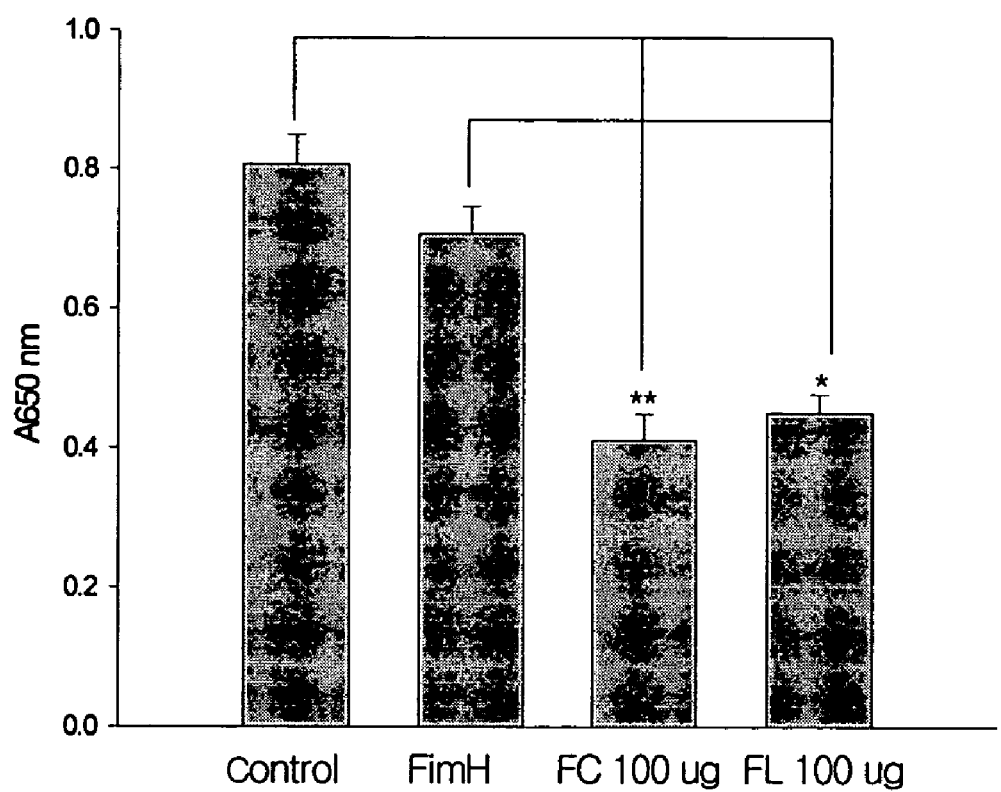
FIG. 18 shows results of MPO assay as a histopathological study for quantification of neutrophils, as one of immune cells most quickly infiltrating infection sites, in the bladder mucosal layer of female BALB/c mice the bladder of which has been then directly injected with the E. coli via the urinary tract and which has been then immunized by oral administration with FimH/CTXA2B or FimH/LTXA2B chimeric proteins to investigate therapeutic effect of the chimeric proteins against E. coli urinary tract infections.

MPO Assay for Evaluation of the Therapeutic Efficacy of the FimH/CTXA2B and FimH/LTXA2B Chimeric Proteins MPO assay was carried out according to the same method as in Example 13. As a result, compared to a control group, both groups administered with FimH/CTXA2B and FimH/LTXA2B chimeric proteins showed a significant reduction in the number of neutrophils (FIG. 18). These results indicate that the FimH/CTXA2B and FimH/LTXA2B chimeric proteins have a potential to be used for therapeutic purposes against urinary tract infections caused by *E. coli*. When uropathogenic *E. coli* infects the urinary tract, a large number of neutrophils and leukocytes in blood vessels in the bladder mucosal region gather at the infection sites, and immune responses are increased at the sites by the immune cells, leading to serious inflammation and eventually tissue damage. In this situation, a reduction in the number of neutrophils indicates that a substance administered has preventive effect against the infection.

As described hereinbefore, the recombinant chimeric protein is useful as an oral vaccine with mild side effects and excellent vaccination efficiency against uropathogenic *E. coli*. Thus, the chimeric vaccine protein can remarkably reduce recurrence of urinary tract infections, prevent occurrence of antibiotic-resistant bacteria by antibiotic abuse, and replace the conventional chemotherapy for urinary tract infections. Also, the chimeric vaccine protein has other advantages of being capable of being produced and commercialized in a short period with relatively low costs, and being easily modified by replacing its genetic constituents with other genes to provide various vaccines.

Although a preferred embodiment of the present invention has been described for illustrative purposes, those skilled in the art will appreciate that various modifications, additions and substitutions are possible, without departing from the scope and spirit of the invention as disclosed in the accompanying claims.

What is claimed is:

1. A recombinant DNA wherein a gene encoding an antigenic determinant of *Escherichia coli* is connected to a CTXA2B gene of *Vibrio cholerae*.

2. A recombinant DNA wherein a gene encoding an antigenic determinant of *Escherichia coli* is connected to a LTXA2B gene of *Escherichia coli*.

3. The recombinant DNA as set forth in claim 1 or 2, wherein the gene encoding the antigenic determinant is FimH.

4. An expression plasmid comprising the recombinant DNA of claim 1 or 2.

5. A recombinant DNA comprising a nucleotide sequence encoding the FimH/CTXA2B chimeric protein of SEQ ID NO:3.

6. A recombinant DNA comprising a nucleotide encoding the FimH/LTXA2B chimeric protein of SEQ ID NO:6.

7. An expression plasmid comprising the nucleotide sequence of claim 4 or 5.

8. The expression plasmid as set forth in claim 7, wherein the recombinant DNA is cloned into the vector pMAL-p2E.

9. An isolated transformed microorganism comprising the expression plasmid of claim 7.

10. The transformed microorganism as set forth in claim 9, wherein the microorganism is *Escherichia coli*.

11. The transformed microorganism as set forth in claim 10, which is *Escherichia coli* PSC KCCM-10553 or *Escherichia coli* PSL KCCM-10552.

12. A vaccine protein consisting of the amino acid sequence of SEQ ID NO:4.

13. A vaccine protein consisting of the amino acid sequence of SEQ ID NO:5.

14. A recombinant DNA comprising a nucleotide sequence encoding the FimH/LTXA2B chimeric protein which consists of nucleotides 1–1100 of SEQ ID NO:1 in FIG. 1 and nucleotides 1–375 of SEQ ID NO:2 in FIG. 1.

* * * * *

SEQUENCE LISTING

```
<160> NUMBER OF SEQ ID NOS: 6

<210> SEQ ID NO 1
<211> LENGTH: 1104
<212> TYPE: DNA
<213> ORGANISM: Artificial Sequence
<220> FEATURE:
<223> OTHER INFORMATION: Description of Artificial Sequence: Synthetic
      LTX One DNA Sequence

<400> SEQUENCE: 1
attgtaatga aacgagttat taccctgttt gctgtactgc tgatgggctg gtcggtaaat      60
gcctggtcat tcgcctgtaa aaccgccaat ggtaccgcta tccctattgg cggtggcagc     120
```

```
gccaatgttt atgtaaacct tgcgcccgtc gtgaatgtgg ggcaaaacct ggtcgtggat      180
ctttcgacgc aaatcttttg ccataacgat tatccggaaa ccattacaga ctatgtcaca      240
ctgcaacgag gctcggctta tggcggcgtg ttatctaatt tttccgggac cgtaaaatat      300
agtggcagta gctatccatt tcctaccacc agcgaaacgc cgcgcgttgt ttataattcg      360
agaacggata agccgtggcc ggtggcgctt tatttgacgc ctgtgagcag tgcgggcggg      420
gtggcgatta aagctggctc attaattgcc gtgcttattt tgcgacagac caacaactat      480
aacagcgatg atttccagtt tgtgtggaat atttacgcca ataatgatgt ggtggtgcct      540
actggcggct gcgatgtttc tgctcgtgat gtcaccgtta ctctgccgga ctaccctggt      600
tcagtgccaa ttcctcttac cgtttattgt gcgaaaagcc aaaacctggg gtattacctc      660
tccggcacaa ccgcagatgc gggcaactcg attttcacca ataccgcgtc gttttcacct      720
gcacagggcg tcggcgtaca gttgacgcgc aacggtacga ttattccagc gaataacacg      780
gtatcgttag gagcagtagg gacttcggcg gtgagtctgg gattaacggc aaattatgca      840
cgtaccggag ggcaggtgac tgcagggaat gtgcaatcga ttattggcgt gacttttgtt      900
tatcaagaag aaccctggat tcatcatgca ccacaaggtt gtggaaattc atcaagaaca      960
attacaggtg atacttgtaa tgaggagacc cagaatctga gcacaatata tctcaggaaa     1020
tatcaatcaa aagttaagag gcagatattt tcagactatc agtcagaggt tgacatatat     1080
aacagaattc ggaatgaatt atga                                            1104

<210> SEQ ID NO 2
<211> LENGTH: 375
<212> TYPE: DNA
<213> ORGANISM: Artificial Sequence
<220> FEATURE:
<223> OTHER INFORMATION: Description of Artificial Sequence: Synthetic
      LTX Two DNA Sequence

<400> SEQUENCE: 2
atgaataaag taaaatgtta tgttttattt acggcgttac tatcctctct atgtgcatac       60
ggagctcccc agtctattac agaactatgt tcggaatatc gcaacacaca aatatatacg      120
ataaatgaca agatactatc atatacggaa tcgatggcag gcaaaagaga aatggttatc      180
attacattta agagcggcgc aacatttcag gtcgaagtcc cgggcagtca acatatagac      240
tcccaaaaaa aagccattga aaggatgaag gacacattaa gaatcacata tctgaccgag      300
accaaaattg ataaattatg tgtatggaat aataaaaccc ccaattcaat tgcggcaatc      360
agtatggaaa actag                                                       375

<210> SEQ ID NO 3
<211> LENGTH: 1475
<212> TYPE: DNA
<213> ORGANISM: Artificial Sequence
<220> FEATURE:
<223> OTHER INFORMATION: Description of Artificial Sequence: Synthetic
      CTX DNA Sequence

<400> SEQUENCE: 3
attgtaatga aacgagttat taccctgttt gctgtactgc tgatgggctg gtcggtaaat       60
gcctggtcat tcgcctgtaa aaccgccaat ggtaccgcta tccctattgg cggtggcagc      120
gccaatgttt atgtaaacct tgcgcccgtc gtgaatgtgg ggcaaaacct ggtcgtggat      180
ctttcgacgc aaatcttttg ccataacgat tatccggaaa ccattacaga ctatgtcaca      240
ctgcaacgag gctcggctta tggcggcgtg ttatctaatt tttccgggac cgtaaaatat      300
```

```
agtggcagta gctatccatt tcctaccacc agcgaaacgc cgcgcgttgt ttataattcg    360
agaacggata agccgtggcc ggtggcgctt tatttgacgc ctgtgagcag tgcgggcggg    420
gtggcgatta agctggctc attaattgcc gtgcttattt tgcgacagac caacaactat    480
aacagcgatg atttccagtt tgtgtggaat atttacgcca ataatgatgt ggtggtgcct    540
actggcggct gcgatgtttc tgctcgtgat gtcaccgtta ctctgccgga ctaccctggt    600
tcagtgccaa ttcctcttac cgtttattgt gcgaaaagcc aaaacctggg gtattacctc    660
tccggcacaa ccgcagatgc gggcaactcg attttcacca ataccgcgtc gttttcacct    720
gcacagggcg tcggcgtaca gttgacgcgc aacggtacga ttattccagc gaataacacg    780
gtatcgttag gagcagtagg gacttcggcg gtgagtctgg gattaacggc aaattatgca    840
cgtaccggag ggcaggtgac tgcagggaat gtgcaatcga ttattggcgt gacttttgtt    900
tatcaagaag agccgtggat tcatcatgca ccgccgggtt gtgggaatgc tccaagatca    960
tcgatgagta atacttgcga tgaaaaaacc caaagtctag gtgtaaaatt ccttgacgaa   1020
taccaatcta aagttaaaag acaaatattt tcaggctatc aatctgatat tgatacacat   1080
aatagaatta aggatgaatt atgattaaat taaaatttgg tgttttttt acagttttac    1140 tatcttcagc atatgcacat ggaacaccte aaaatattac tgatttgtgt gcagaatacc    1200
acaacacaca aatacatacg ctaaatgata agatattttc gtatacagaa tctctagctg    1260
gaaaaagaga gatggctatc attacttta agaatggtgc aacttttcaa gtagaagtac    1320
caggtagtca acatatagat tcacaaaaaa agcgattga aaggatgaag gatacccctga   1380 ggattgcata tcttactgaa gctaaagtcg aaaagttatg tgtatggaat aataaaacgc    1440
ctcatgcgat tgccgcaatt agtatggcaa attaa                              1475
```

<210> SEQ ID NO 4
<211> LENGTH: 491
<212> TYPE: PRT
<213> ORGANISM: Artificial Sequence
<220> FEATURE:
<223> OTHER INFORMATION: Description of Artificial Sequence: Synthetic
      LTX Amino Acid Sequence

<400> SEQUENCE: 4

```
Ile Val Met Lys Arg Val Ile Thr Leu Phe Ala Val Leu Leu Met Gly
  1               5                  10                  15

Trp Ser Val Asn Ala Trp Ser Phe Ala Cys Lys Thr Ala Asn Gly Thr
             20                  25                  30

Ala Ile Pro Ile Gly Gly Gly Ser Ala Asn Val Tyr Val Asn Leu Ala
         35                  40                  45

Pro Val Val Asn Val Gly Gln Asn Leu Val Val Asp Leu Ser Thr Gln
     50                  55                  60

Ile Phe Cys His Asn Asp Tyr Pro Glu Thr Ile Thr Asp Tyr Val Thr
 65                  70                  75                  80

Leu Gln Arg Gly Ser Ala Tyr Gly Gly Val Leu Ser Asn Phe Ser Gly
                 85                  90                  95

Thr Val Lys Tyr Ser Gly Ser Ser Tyr Pro Phe Pro Thr Thr Ser Glu
            100                 105                 110

Thr Pro Arg Val Val Tyr Asn Ser Arg Thr Asp Lys Pro Trp Pro Val
        115                 120                 125

Ala Leu Tyr Leu Thr Pro Val Ser Ser Ala Gly Gly Val Ala Ile Lys
    130                 135                 140
```

```
Ala Gly Ser Leu Ile Ala Val Leu Ile Leu Arg Gln Thr Asn Asn Tyr
145                 150                 155                 160

Asn Ser Asp Asp Phe Gln Phe Val Trp Asn Ile Tyr Ala Asn Asn Asp
                165                 170                 175

Val Val Val Pro Thr Gly Gly Cys Asp Val Ser Ala Arg Asp Val Thr
            180                 185                 190

Val Thr Leu Pro Asp Tyr Pro Gly Ser Val Pro Ile Pro Leu Thr Val
        195                 200                 205

Tyr Cys Ala Lys Ser Gln Asn Leu Gly Tyr Tyr Leu Ser Gly Thr Thr
    210                 215                 220

Ala Asp Ala Gly Asn Ser Ile Phe Thr Asn Thr Ala Ser Phe Ser Pro
225                 230                 235                 240

Ala Gln Gly Val Gly Val Gln Leu Thr Arg Asn Gly Thr Ile Ile Pro
                245                 250                 255

Ala Asn Asn Thr Val Ser Leu Gly Ala Val Gly Thr Ser Ala Val Ser
            260                 265                 270

Leu Gly Leu Thr Ala Asn Tyr Ala Arg Thr Gly Gly Gln Val Thr Ala
        275                 280                 285

Gly Asn Val Gln Ser Ile Ile Gly Val Thr Phe Val Tyr Gln Glu Glu
    290                 295                 300

Pro Trp Ile His His Ala Pro Gln Gly Cys Gly Asn Ser Ser Arg Thr
305                 310                 315                 320

Ile Thr Gly Asp Thr Cys Asn Glu Glu Thr Gln Asn Leu Ser Thr Ile
                325                 330                 335

Tyr Leu Arg Lys Tyr Gln Ser Lys Val Lys Arg Gln Ile Phe Ser Asp
            340                 345                 350

Tyr Gln Ser Glu Val Asp Ile Tyr Asn Arg Ile Arg Asn Glu Leu Met
        355                 360                 365

Asn Lys Val Lys Cys Tyr Val Leu Phe Thr Ala Leu Leu Ser Ser Leu
    370                 375                 380

Cys Ala Tyr Gly Ala Pro Gln Ser Ile Thr Glu Leu Cys Ser Glu Tyr
385                 390                 395                 400

Arg Asn Thr Gln Ile Tyr Thr Ile Asn Asp Lys Ile Leu Ser Tyr Thr
                405                 410                 415

Glu Ser Met Ala Gly Lys Arg Glu Met Val Ile Ile Thr Phe Lys Ser
            420                 425                 430

Gly Ala Thr Phe Gln Val Glu Val Pro Gly Ser Gln His Ile Asp Ser
        435                 440                 445

Gln Lys Lys Ala Ile Glu Arg Met Lys Asp Thr Leu Arg Ile Thr Tyr
    450                 455                 460

Leu Thr Glu Thr Lys Ile Asp Lys Leu Cys Val Trp Asn Asn Lys Thr
465                 470                 475                 480

Pro Asn Ser Ile Ala Ala Ile Ser Met Glu Asn
                485                 490
```

<210> SEQ ID NO 5
<211> LENGTH: 491
<212> TYPE: PRT
<213> ORGANISM: Artificial Sequence
<220> FEATURE:
<223> OTHER INFORMATION: Description of Artificial Sequence: Synthetic
      CTX Amino Acid Sequence

<400> SEQUENCE: 5

```
Ile Val Met Lys Arg Val Ile Thr Leu Phe Ala Val Leu Leu Met Gly
 1               5                  10                  15
```

-continued

```
Trp Ser Val Asn Ala Trp Ser Phe Ala Cys Lys Thr Ala Asn Gly Thr
             20                  25                  30
Ala Ile Pro Ile Gly Gly Ser Ala Asn Val Tyr Val Asn Leu Ala
         35                  40                  45
Pro Val Val Asn Val Gly Gln Asn Leu Val Val Asp Leu Ser Thr Gln
 50                  55                  60
Ile Phe Cys His Asn Asp Tyr Pro Glu Thr Ile Thr Asp Tyr Val Thr
 65                  70                  75                  80
Leu Gln Arg Gly Ser Ala Tyr Gly Val Leu Ser Asn Phe Ser Gly
                 85                  90                  95
Thr Val Lys Tyr Ser Gly Ser Ser Tyr Pro Phe Pro Thr Thr Ser Glu
            100                 105                 110
Thr Pro Arg Val Val Tyr Asn Ser Arg Thr Asp Lys Pro Trp Pro Val
            115                 120                 125
Ala Leu Tyr Leu Thr Pro Val Ser Ser Ala Gly Gly Val Ala Ile Lys
            130                 135                 140
Ala Gly Ser Leu Ile Ala Val Leu Ile Leu Arg Gln Thr Asn Asn Tyr
145                 150                 155                 160
Asn Ser Asp Asp Phe Gln Phe Val Trp Asn Ile Tyr Ala Asn Asn Asp
                165                 170                 175
Val Val Val Pro Thr Gly Gly Cys Asp Val Ser Ala Arg Asp Val Thr
            180                 185                 190
Val Thr Leu Pro Asp Tyr Pro Gly Ser Val Pro Ile Pro Leu Thr Val
            195                 200                 205
Tyr Cys Ala Lys Ser Gln Asn Leu Gly Tyr Tyr Leu Ser Gly Thr Thr
            210                 215                 220
Ala Asp Ala Gly Asn Ser Ile Phe Thr Asn Thr Ala Ser Phe Ser Pro
225                 230                 235                 240
Ala Gln Gly Val Gly Val Gln Leu Thr Arg Asn Gly Thr Ile Ile Pro
                245                 250                 255
Ala Asn Asn Thr Val Ser Leu Gly Ala Val Gly Thr Ser Ala Val Ser
            260                 265                 270
Leu Gly Leu Thr Ala Asn Tyr Ala Arg Thr Gly Gly Gln Val Thr Ala
            275                 280                 285
Gly Asn Val Gln Ser Ile Ile Gly Val Thr Phe Val Tyr Gln Glu Glu
            290                 295                 300
Pro Trp Ile His His Ala Pro Pro Gly Cys Gly Asn Ala Pro Arg Ser
305                 310                 315                 320
Ser Met Ser Asn Thr Cys Asp Glu Lys Thr Gln Ser Leu Gly Val Lys
                325                 330                 335
Phe Leu Asp Glu Tyr Gln Ser Lys Val Lys Arg Gln Ile Phe Ser Gly
            340                 345                 350
Tyr Gln Ser Asp Ile Asp Thr His Asn Arg Ile Lys Asp Glu Leu Met
            355                 360                 365
Ile Lys Leu Lys Phe Gly Val Phe Phe Thr Val Leu Leu Ser Ser Ala
            370                 375                 380
Tyr Ala His Gly Thr Pro Gln Asn Ile Thr Asp Leu Cys Ala Glu Tyr
385                 390                 395                 400
His Asn Thr Gln Ile His Thr Leu Asn Asp Lys Ile Phe Ser Tyr Thr
                405                 410                 415
Glu Ser Leu Ala Gly Lys Arg Glu Met Ala Ile Ile Thr Phe Lys Asn
            420                 425                 430
```

-continued

```
Gly Ala Thr Phe Gln Val Glu Val Pro Gly Ser Gln His Ile Asp Ser
        435                 440                 445

Gln Lys Lys Ala Ile Glu Arg Met Lys Asp Thr Leu Arg Ile Ala Tyr
    450                 455                 460

Leu Thr Glu Ala Lys Val Glu Lys Leu Cys Val Trp Asn Asn Lys Thr
465                 470                 475                 480

Pro His Ala Ile Ala Ala Ile Ser Met Ala Asn
                485                 490

<210> SEQ ID NO 6
<211> LENGTH: 1475
<212> TYPE: DNA
<213> ORGANISM: Artificial Sequence
<220> FEATURE:
<223> OTHER INFORMATION: Description of Artificial Sequence: Synthetic
      LTX DNA sequence

<400> SEQUENCE: 6
attgtaatga aacgagttat taccctgttt gctgtactgc tgatgggctg gtcggtaaat    60
gcctggtcat tcgcctgtaa aaccgccaat ggtaccgcta tccctattgg cggtggcagc   120
gccaatgttt atgtaaacct tgcgcccgtc gtgaatgtgg ggcaaaacct ggtcgtggat   180
cttttcgacg aaatcttttg ccataacgat tatccggaaa ccattacaga ctatgtcaca   240
ctgcaacgag gctcggctta tggcggcgtg ttatctaatt tttccgggac cgtaaaatat   300
agtggcagta gctatccatt tcctaccacc agcgaaacgc cgcgcgttgt ttataattcg   360
agaacggata agccgtggcc ggtggcgctt tatttgacgc ctgtgagcag tgcgggcggg   420
gtggcgatta aagctggctc attaattgcc gtgcttattt tgcgacagac caacaactat   480
aacagcgatg atttccagtt tgtgtggaat atttacgcca ataatgatgt ggtggtgcct   540
actggcggct gcgatgtttc tgctcgtgat gtcaccgtta ctctgccgga ctaccctggt   600
tcagtgccaa ttcctcttac cgtttattgt gcgaaaagcc aaaacctggg gtattacctc   660
tccggcacaa ccgcagatgc gggcaactcg attttcacca ataccgcgtc gttttcacct   720
gcacagggcg tcggcgtaca gttgacgcgc aacggtacga ttattccagc gaataacacg   780
gtatcgttag gagcagtagg gacttcggcg gtgagtctgg gattaacggc aaattatgca   840
cgtaccggag ggcaggtgac tgcagggaat gtgcaatcga ttattggcgt gacttttgtt   900
tatcaagaag aaccctggat tcatcatgca ccacaaggtt gtggaaattc atcaagaaca   960
attacaggtg atacttgtaa tgaggagacc cagaatctga gcacaatata tctcaggaaa  1020
tatcaatcaa aagttaagag gcagatattt tcagactatc agtcagaggt tgacatatat  1080
aacagaattc ggaatgaatt atgaataaag taaaatgtta tgttttattt acggcgttac  1140
tatcctctct atgtgcatac ggagctcccc agtctattac agaactatgt tcggaatatc  1200
gcaacacaca aatatatacg ataaatgaca agatactatc atatacggaa tcgatggcag  1260
gcaaaagaga aatggttatc attacatttta agagcggcgc aacatttcag gtcgaagtcc  1320
cgggcagtca acatatagac tcccaaaaaa aagccattga aaggatgaag gacacattaa  1380
gaatcacata tctgaccgag accaaaattg ataaattatg tgtatggaat aataaaaccc  1440
ccaattcaat tgcggcaatc agtatggaaa actag                              1475
```